United States Patent [19]
Lipsky et al.

[11] Patent Number: 5,294,443
[45] Date of Patent: Mar. 15, 1994

[54] TRIPTERYGIUM WILFORD II HOOK F EXTRACTS AND COMPONENTS THEREOF FOR IMMUNOSUPPRESSION

[75] Inventors: Peter E. Lipsky; Xue-Lian Tao, both of Dallas, Tex.

[73] Assignee: Board of Regents, The University of Texas System, Austin, Tex.

[21] Appl. No.: 862,836

[22] Filed: Apr. 3, 1992

Related U.S. Application Data

[63] Continuation-in-part of Ser. No. 494,113, Mar. 14, 1990, abandoned.

[51] Int. Cl.$^5$ .............................................. A61K 35/78
[52] U.S. Cl. .................................. 424/195.1; 514/885
[58] Field of Search ...................... 424/195.1; 514/885

[56]        References Cited
        U.S. PATENT DOCUMENTS

| | | | |
|---|---|---|---|
| 4,005,108 | 1/1977 | Kupchan et al. | 549/297 |
| 4,241,536 | 12/1980 | Saint-Firmin | 47/58 |
| 4,328,309 | 5/1982 | Chalmers et al. | 435/126 |

OTHER PUBLICATIONS

Weijiang et al., "Studies on Diterpenoids from Tripterygium Wilfordii," *Acta Academiae Medicinae Shanghai*, 13(4): 272, 1986, published in China.

Kupchan et al., "Triptolide and Tripdiolide, Novel Anitleukemic Diterpenoid Triepoxides from Tripterygium wilfordii," *Journal of the American Chemical Society*, 94(20): 7194–7195, 1972, published in U.S.A.

Zhang et al., "Antineoplastic Action of Triptolide and its Effect on the Immunologic Functions in Mice," *Acta Pharmacologica Sinica*, 2(2): 128–131, 1981, published in China.

Wenyan et al., "Tripterygium in Dermatologic Therapy," *International Journal of Dermatology*, 24(3): 152–157, 1985, published in U.S.A.

Deng et al., "The Structure of Triptodihydroxy Acid Methyl Ester and Wilfortrine," *Chemical Abstracts*, 107: 436, #55718y, 1987, published in Columbus, Ohio.

Wu et al., "The Crystal Structure of Triptophenolide Methyl Ether," *Chemical Abstracts*, 107: 712, #96914c, 1987, published in Columbus, Ohio.

He et al., "Structures of Wilforgine, Wilforzine and Wilformine from Tripterygium Wilfordii," *Chemical Abstracts*, 107:422, #130906p, 1987, published in Columbus, Ohio.

Deng et al., "The Isolation and Structure of Triptonoterpenol," *Chemical Abstracts*, 107:369, #112684k, 1987, published in Columbus, Ohio.

PCT search report dated Aug. 16, 1991 published in Europe.

Pu & Zhang, "Effects of Triptolide on T Lymphocyte Functions in Mice," *Chemical Abstracts, Pharmacology*, 112:45, #171972d, 1990, published Columbus, Ohio.

Bai et al., "Tripterygium Wilfordii Hook F in Treatment of Rheumatoid Arthritis and Ankylosing Spondylitis,"*Biological Abstracts*, 87(3), #29969, 1989, published in U.S.A.

Zheng et al., "Immonosuppressive Effects of Wilfortrine and Euonine," *Chemical Abstracts*, 112(3):22, #16029h, 1990, published in Columbus, Ohio.

Zhang et al., "Antineoplastic Effect of Triptolide and its Effect on the Immunologic Functions in Mice,"

(List continued on next page.)

*Primary Examiner*—John W. Rollins
*Attorney, Agent, or Firm*—Arnold, White & Durkee

[57]        ABSTRACT

The present invention involves the use of *Tripterygium Wilfordii Hook F* extracts in the treatment of rheumatoid arthritis. An alcohol extract of this plant (T2) inhibited antigen- and mitogen-stimulated proliferation of T cells and B cells, cell cycle progression, interleukin-2 (IL-2) production by T cells, immunoglobulin production by B cells and interleukin-2 mRNA production. T2 did not affect IL-2 receptor expression by T cells, IL-1 production by monocytes, the capacity of monocytes to present antigen, or signaling pathways. Inhibition could not be accounted for by nonspecific toxicity. These results support the conclusion that T2 exerts a powerful suppressive effect on human immune responses. Suppressing autoinnune disease is a most preferred embodiment of this invention.

10 Claims, 14 Drawing Sheets

OTHER PUBLICATIONS

Chemical Abstracts, 95(9):102, #73690w, 1981 published in Columbus, Ohio.

Xia & Chen, "Alkaloids from Stems and Leaves of Tripterygium Wilfordii," Chemical Abstracts, 113(25):38, #224305t, 1990, published in Columbus, Ohio.

Tripterygium Wilfordii Hook Research Group, "Studies on Total Glycosides of Tripterygium Wilfordii on Dermatoses," Biological Abstracts, 7979(9):762, #80151, 1985, published in U.S.A.

Chang et al., "A Preliminary Study on the Immunosuppressive Activity of Mixed Glycoside of T. Wilfordii," Biological Abstracts, 79(10), #89135, 1985, published in U.S.A.

Li & Weir, "Radix T. wilfordii: A Chinese Herbal Medicine with Potent Immunosuppressive Properties," Biological Abstracts, 90(7), #79317, 1990, published in U.S.A.

Wang & Yuan, "A Tablet of Tripterygium Wilfordii in Treating Lupus Erythematosus," Chung Hsi I Chieh Ho Tsa Chih (China), 9(7):389–407, 1989, published in China.

Xu et al., "Tripterygium in Dermatologic Therapy," Int. J. Dermatol., 24(3):152–157, 1985, published in U.S.A.

Su et al., "Comparative Clinical Study of Rheumatoid Arthritis Treated by Triptolide and an Ethyl Acetate Extract of Tripterygium Wilfordii," Chung Hsi I Chieh Ho Tsa Chih (China), 10(3):131 & 144–146, 1990, published in China.

Tao et al., "A Prospective, Controlled, Double-blind, Cross-over Study of Tripterygium wilfordii Hook F in Treatment of rheumatoid Arthritis," Chin. Med. J. published in (China), 102(5):327–332, 1989, published in China.

Tao et al., "Effect of an Extract of the Chinese Herbal Remedy Tripterygium Wilfordii Hook F on Human Immune Responsiveness," Arthritis and Rheumatism, 34(10):1274–1281, 1991, published in U.S.A.

Chen et al., (1987) "Clinical analysis of 10 cases of Tripterygium wilfordii Hook caused toxicity" Symposium, Clinical Application of Tripterygium wilfordii Hook, Hubei, China, published in China.

Zheng et al., (1983) "Studies on toxicity of totla glycosides in Tripterygium wilfordii" Acta. Acad. Med. Sinicae 5(2):73, published in China.

Zheng et al., (1983) "Studies on pharmacological actions of total glycosides in Tripterygium wilfordii Hook F" Acta. Acad. Med. Sinicae 5:1, published in China.

Chang et al., (1984) "A preliminary study of the immunosuppressive activity of mixed glycosides of Tripterygium wilfordii Hook F" Chinese J. Immunol. 4:331, published in China.

Zheng et al., (1982) "Effect of the decoction of Tripterygium wilfordii Hook on immune functions" Fujiang Med. J. 4:222, published in China.

Zuo et al., (1986) "Different effect of Tripterygium reglii on T and B cell function" Chinese J. Immunol. 2:232, published in China.

Jia Li (1985) "Chemistry and pharmacology and clinical application of plants of Tripterygium family" Yao Xue Tong Bao 20:101, published in China.

Tao et al., (1987) "Prospective, controlled, double-blind, cross-over trial of T2 (polyglycosides extracted from Tripterygium wilfordii Hook F) in the treatment of rheumatoid arthritis" Chinese J. Int. Med. 26:399, published in China.

Tao et al., (1988) "Mechanism of treatment of rheumatoid arthritis with Tripterygium wilfordii Hook F I. Effect of T2 on secretion of total IgM and IgM-RF by PBMC" Acta. Acad. Med. Sinicae 10:361, published in China.

Hubei Study Group (1982) "Pharmacological study on the ethanol extract of Tripterygium wilfordii Hook F" Zung Cao Yao 13:27, published in China.

Wei et al., (1988) "Side effects of T2 in the treatment of 106 patients with glomerular diseases" New Drug and It's Clinical Application 1(6):37, published in China.

Jiang et al., (1987) "Tripterygium wilfordii Hook caused acute toxicity with kidney involvement in 17 cases" Chinese J. Kidney Dis 3(3):167, published in China.

Zhang, LS (1986) "Inhibitory effect of celastrol on murine lymphocyte proliferation" Acta. Pharmacol. Sinicae 7:85, published in China.

Kupchan, SM (1976) "Novel plant-derived tumor inhibitors and their mechanisms of action" Cancer Treatment Reports 60:1115, published in U.S.A.

Zhang et al., (1986) "Studies on Diterpenoids from Tripterygium wilfordii," Shanghai Yike Da ue Zuebao 13(4);267–272, published in Chemical Abstracts, Columbus, Ohio.

Kupchan et al., (1972), "Triptolide and Tripdiolide, Novel Antileukemic Diterpenoid Triepoxides from Tripterygium wilfordii," J. Am. Chem. Soc., 94:7194–7195, published in U.S.A.

1, R= H
2, R= OH

3

1, R = OH
2, R = Me

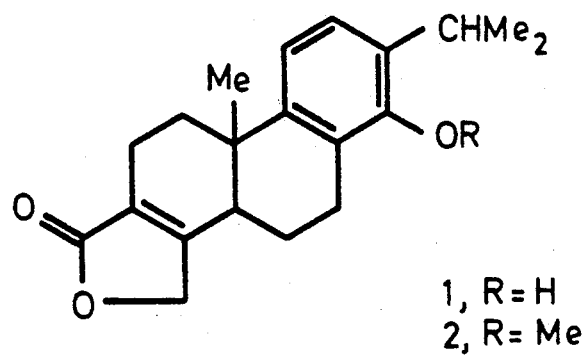
1, R= H
2, R= Me
FIG.16
FIG.17
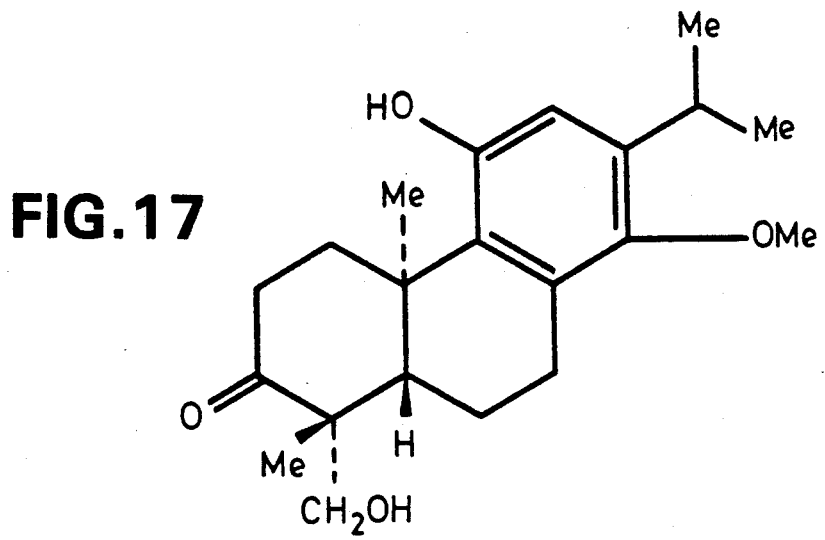
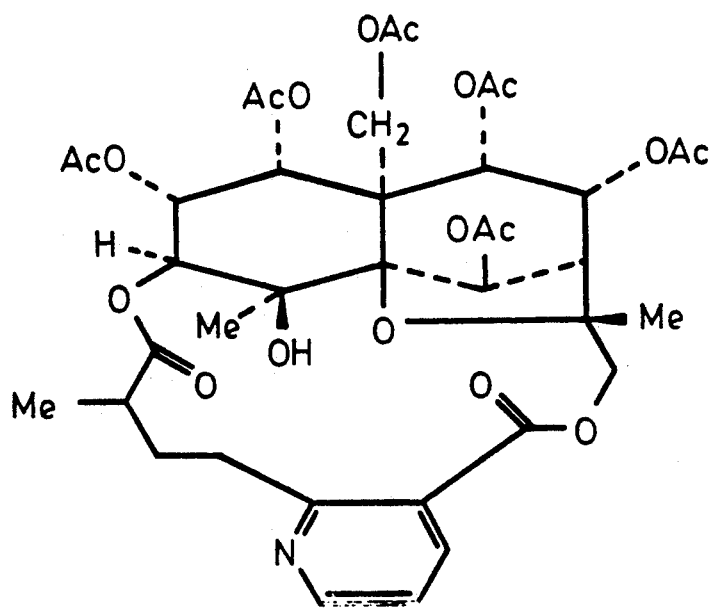
FIG.18

TRIPTERYGIUM WILFORD II HOOK F EXTRACTS AND COMPONENTS THEREOF FOR IMMUNOSUPPRESSION

The government has rights in the present invention as research relevant to the development thereof was supported by a grant from the United States government, NIH grant AR-36169.

This application is a continuation-in-part of application Ser. No. 07/494,113 filed Mar. 14, 1990, now abandoned.

BACKGROUND OF THE INVENTION

Rheumatoid arthritis (RA) is a chronic inflammatory disease of uncertain etiology (1,2). Since the cause is unknown, treatment has been directed at suppressing the signs and symptoms of chronic inflammation. Although many agents have been documented to decrease pain and swelling temporarily, none has been shown to have a major impact on the course of the disease. New therapeutic modalities have been developed over the past few years, employing monoclonal antibodies, cytokine antagonists, specific receptor targeted toxins, and other biologics (3-17). Nevertheless, uniform and persistent suppression of disease activity has not been reported. Although these approaches remain promising, alternative means of drug development seen warranted and could yield not only new and effective treatment modalities, but also provide new insights into disease pathogenesis that could serve as the basis of future therapeutic innovations.

An area to search for new therapeutic interventions for RA is that of traditional Chinese medicines. One of these traditional medicines is from *Tripterygium wilfordii Hook F*, a shrub-like vine from the Celastraceae family (18). A variety of preparations derived from this plant have been used in South China for many years to treat different forms of arthritis and other autoimmune diseases. In 1978, an extract of *Tripterygium wilfordii Hook F* was produced by chloroform reethanol extraction of the woody portion of the roots and designated T2 (18). Reports in the Chinese literature describe T2 treatment of more than 750 patients with a variety of autoimmune diseases (19-35). The general impression has been that T2 is well-absorbed orally, appears to have acceptable toxicity, and is effective in the treatment of various autoimmune diseases.

T2 was evaluated in a double-blind placebo controlled cross-over study involving 70 RA patients, with a mean disease duration of 6 years (19-20). Statistically significant improvement in all clinical parameters, particularly ESR, CRP, and Rheumatoid factor titers, was noted after 12 weeks of therapy in the experimental group compared with either baseline measurements or the placebo treated group. Of the patients treated, 82-93% noted improvement in different clinical criteria or laboratory correlates of inflammation. An immunosuppressive activity was implicated by the finding that treatment induced inhibition of the production of IgM and IgM rheumatoid factor by the patients' peripheral blood mononuclear cells in vitro (20). Toxicity, which consisted primarily of skin rash, gastrointestinal complaints and amenorrhea, was generally mild and reversible with cessation of therapy. These results support the contention that T2 might be an effective therapy for RA, but there is little experience with this agent outside of China.

*Tripterygium wilfordii Hook F* is known to contain a number of constituents, some of which appear to be toxic (36). It is known that the leaves, stem, flowers, and the skin of the roots are poisonous and that ingestion can cause death (37-39). In contrast, the woody portion of the roots of the plant is much less toxic. T2 is prepared from the woody portion of the roots, appears to contain the therapeutic components, and to have reduced toxicity compared with other preparations.

The Chinese experience has suggested that a daily dosage of 0.8-1.5 mg/kg of T2 is safe and effective. Acute and chronic toxicity studies have been carried out in China using a variety of animal models. The $LD_{50}$ in mice is $159.7 \pm 14.3$ mg/kg (40). The major chronic toxicity noted in rats administered 30 mg/kg for 90 days was azoospermia and decrease in testicular weight (40). Lower dosages of T2 did not cause decreases in testicular weight. The toxicity studies, therefore, suggest that T2 exhibits a reasonable safety index and should be able to be administered to patients safely.

Research has begun in China to determine the spectrum of activity of T2. Triptonide and triptolide from this plant have been reported to inhibit the proliferation of lymph cells induced by concanavalin A. ((Zhang et al., Shanghai Yike Da ue Xuebao, 1986, 13 (4) pp. 267-272.)) Additionally, ancient Chinese medical books have suggested that this herbal remedy is useful to treat joint pain. Recently, this extract has been used in the treatment of rheumatic diseases including rheumatoid arthritis, as well as systemic lupus erythematosus, Behcet's disease, and psoriasis. Alcoholic extracts (T2) of the plant have been described as having significant activity in vivo against certain mouse leukemias and in vitro against cells derived from human carcinomas (Kupchan et al., J. An. Chem. Soc., 1972, 94 pp. 3194-3195). The capacity of T2 to suppress a number of animal models of autoimmune disease, including adjuvant arthritis and experimental allergic encephalomyelitis, has been reported (41-47). Large concentrations of T2 (30 mg/kg) suppress delayed hypersensitivity reactivity in mice and may also suppress graft versus host disease, as well as skin and heart allograft rejection (36,41). In general, however, only very large concentrations of T2 have been examined in these studies. It, therefore, remains unclear whether lower, more pharmacologically appropriate concentrations would also exert therapeutic effects in these animal models.

T2 is a crude extract containing a mixture of materials, including various glycosides, alkaloids, and diterpenoids. The active principle, however, has not yet been identified. A few components have been purified, including triptolide, wilfordine, and related compounds, but proof that a particular purified component accounts for the therapeutic or immunosuppressive activity of T2 does not exist (48).

High concentrations of triptolide were reported to suppress B and T lymphocyte proliferation and interleukin-2 production by mouse spleen cells (Pu et al. (1990) Chem. Abstracts, 112:45, abstract 171972d). The concentrations used were sufficiently high that significant nonspecific toxicity undoubtedly occurred.

SUMMARY OF THE INVENTION

The present invention involves the use of *Tripterygium wilfordii Hook F* extracts (T2) or components thereof to selectively suppress the immunity of an animal or a patient in need of such treatment. Immunity of an animal may include immunoglobulin synthesis, cell proliferation of peripheral blood lymphocytes, cellular immune responses or proliferation of T and B lymphocytes.

In particular, the selective inhibition of interleukin-2 production by inhibition of IL-2 gene transcription and consequent inhibition of IL-2 specific mRNA production without substantial cellular toxicity is an aspect of the present invention. Lack of substantial cellular toxicity is indicated by substantially unchanged interleukin-2 receptor expression or cellular signaling activities such as inositol triphosphate production, diacylglycerol generation, translocation of protein kinase C or protein tyrosine kinase activity. Lack of substantial cellular toxicity by T2 may also ? Rean having little or no effect on the capacity of monocytes to function as antigen presenting cells, having little or no effect on the growth of endothelial cells or fibroblasts, or having little or no effect on the viability of either resting or stimulated lymphocytes, endothelial cells, fibroblasts, monocytes or polymorphonuclear leukocytes.

The administration of Tripterygium wilfordii Hook F T2 extract in a therapeutically effective amount to suppress autoimmune disease in a patient in need of such treatment is a most preferred embodiment of this invention. A therapeutically effective amount of T2 inhibits IL-2 production without substantial cellular toxicity. An in vivo therapeutically effective amount of T2 for humans is about 60 mg/day. An in vitro therapeutically effective amount of T2 for cell cultures is about 1.0 µg/ml. Particular autoimmune diseases thought amenable to such treatment include rheumatoid arthritis, systemic lupus erythematosus and psoriasis.

A method of testing for selective inhibition of IL-2 specific mRNA production is an aspect of the present invention, the method consisting essentially of: culturing eukaryotic cells in culture with and separately without Tripterygium wilfordii Hook F T2 extract or components thereof in a therapeutically effective amount to provide a test sample and a control sample; measuring IL-2 aMA level and a reference mRNA level such as actin mRNA to provide a test IL-2 mRNA sample, a test reference mRNA sample, a control IL-2 mRNA sample and a control reference mRNA sample; comparing (test IL-2 mRNA level ÷ control IL-2 mRNA level) to (test reference mRNA level ÷ control reference mRNA level); wherein when (test IL-2 mRNA level ÷ control IL-2 mRNA level) is substantially less than 1 and (test reference mRNA level ÷ control reference mRNA level) is about 1, selective inhibition of IL-2 mRNA production by T2 is indicated.

The specific T2 impairment of IL-2 mRNA production with nontoxicity to other cellular functions and other cell types is a surprising and unexpected aspect of the present invention. This specificity of T2 can be ascribed to individual or a combination of components of the T2 extract.

| ABBREVIATIONS | |
|---|---|
| CRP = | cross-reacting protein |
| DAG = | diacylglycerol |
| ESR = | erythrocyte sedimentation rate |
| FACS = | fluorescence-activated cell sorter |
| Ig = | immunoglobulin |
| IL-2 = | interleukin-2 |
| IL-2R = | interleukin-2 receptor |
| IP = | phosphatidyl inositol triphosphate |
| MAb = | monoclonal antibodies |
| NHS = | normal human serum |
| PBMC = | peripheral blood mononuclear cells |

| -continued ABBREVIATIONS | |
|---|---|
| PDB = | phorbol dibutyrate |
| PHA = | phytohemagglutinin |
| PKC = | protein kinase C |
| RA = | rheumatoid arthritis |
| SA = | formalinized Staphylococcus aureus |
| SK = | streptokinase |
| SRBC = | sheep red blood cells |
| T2 = | an ethanol extract from the woody portion of Tripterygium wilfordii Hook F |
| TT = | tetanus toxoid |

BRIEF DESCRIPTION OF THE DRAWINGS

In FIG. 6A, B cells ($5 \times 10^4$/well) were stimulated with SA (o) or SA+IL-2 (o), and in FIG. 6B with SA+IL-2 in the presence of varying concentrations of T2. [$^3$H]-TdR was determined after a 5-day incubation (left panel). Supernatants were harvested after a seven-day culture and assayed for IgM (■) and IgG (o) and IgA (o) content (right panel). Results are the mean±SEN of 3 experiments.

FIG. 16 shows the structure of triptophenolide (1) and triptophenolide methyl ester (2).

FIG. 17 schematically shows the structure of triptonoterpenol.

FIG. 18 schematically shows the structure of wilformine.

DESCRIPTION OF PREFERRED EMBODIMENTS

Figure 1:
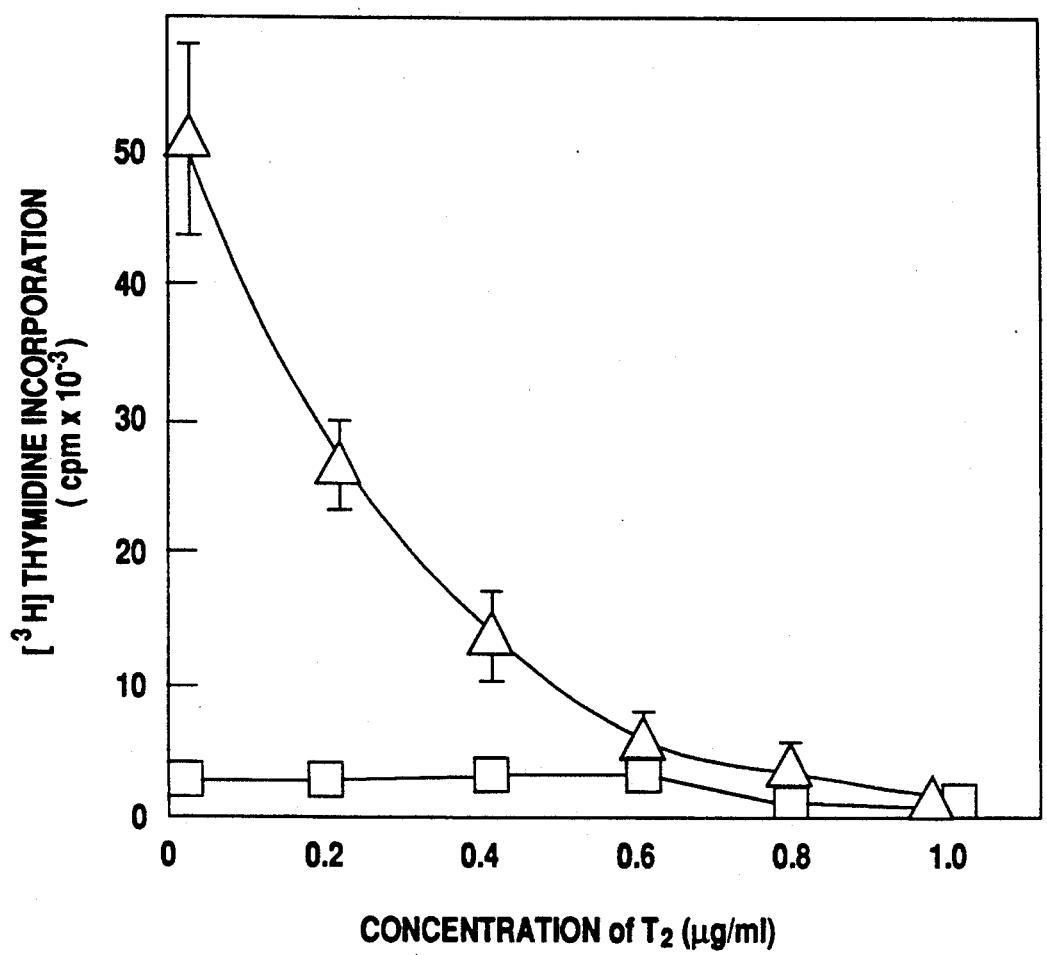
FIG. 1. Effect of T2 on T cell proliferation. T cells ($1 \times 10^5$/well) were cultured with medium (□) or PHA (△) in the presence or absence of varying concentrations of T2 as indicated for 3 days. Results represent the mean cpm±SEM of three experiments.
Figure 2A:
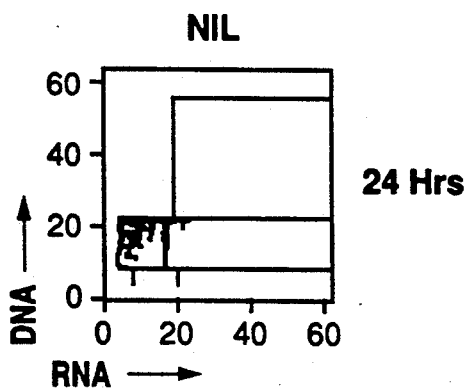
FIGS. 2A–2L. Effect of T2 on cell cycle progression of human T cells. T cells ($1 \times 10^5$/well) were cultured with or without PHA (1 µg/ml) in the absence or presence of the indicated concentrations of T2 for 24, 48 or 72 hrs. The samples were harvested, stained with acridine orange, and analyzed with an ORTHO flow cytometer using the CICERO prograra to determine the position of cells in the cell cycle as assessed by their RNA and DNA content.
Figure 2D:
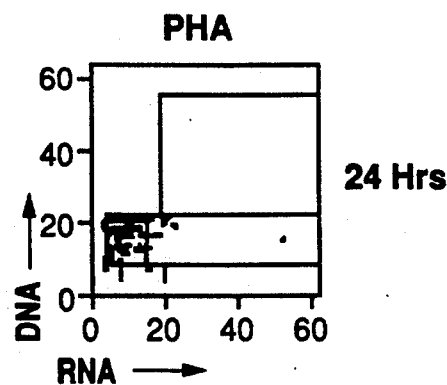
Figure 2B:
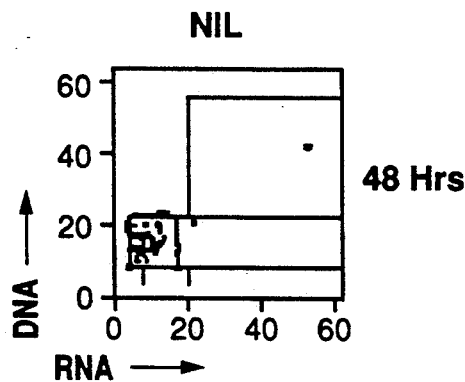
Figure 2E:
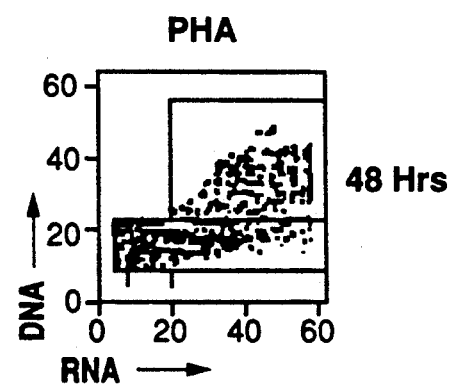
Figure 2C:
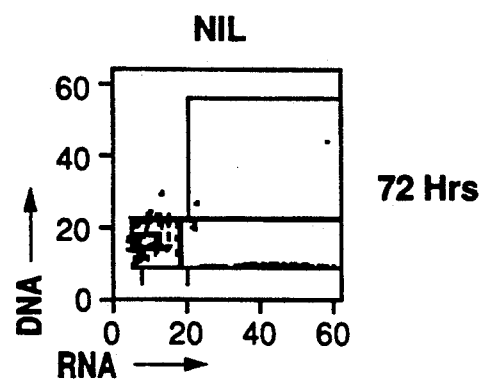
Figure 2F:
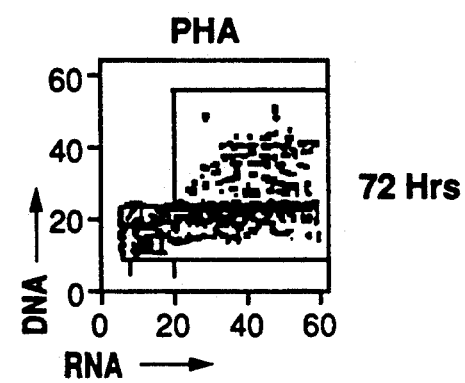
Figure 2G:
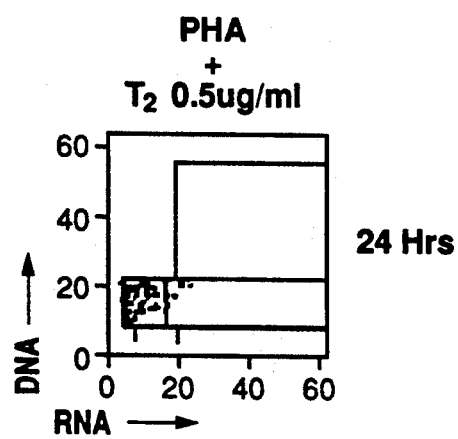
Figure 2J:
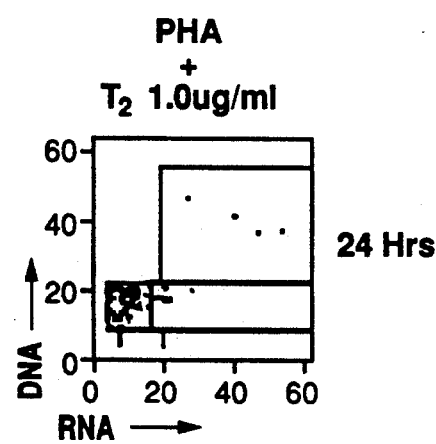
Figure 2H:
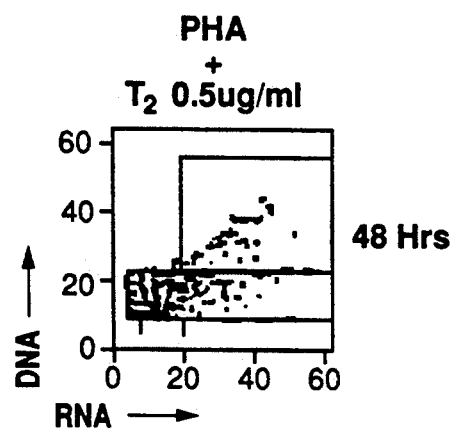
Figure 2K:
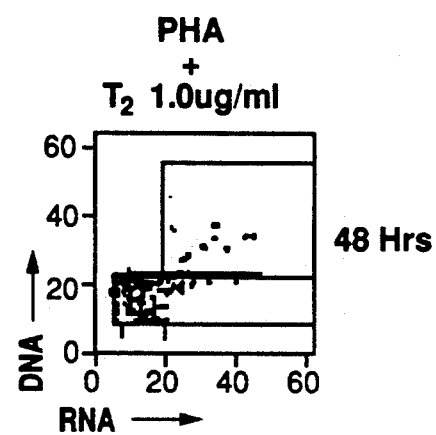
Figure 2I:
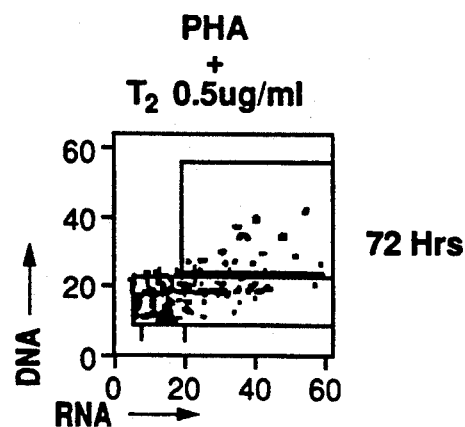
Figure 2L:
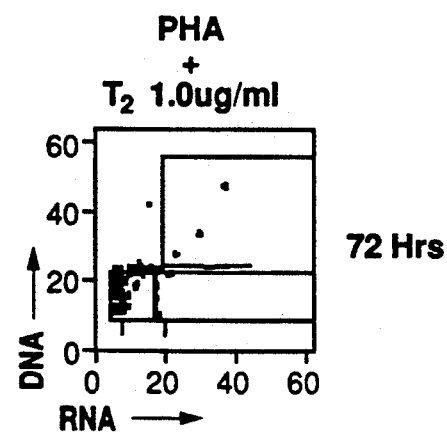

The present invention concerns the use of *Tripterygium wilfordii Hook F* extracts to suppress immune function, particularly for the treatment of autoimmune diseases. T2 was prepared by ethanol extraction of *Triptexygium wilfordii Hook F* roots.

Example 1 concerns studies on the effect of T2 on human lymphocyte function. Interleukin-2 production by T cells is inhibited by T2 due to an inhibition of gene transcription while the expression of IL-2 receptors is not affected. T2 also suppresses proliferation of B cells and immunoglobulin production by B cells. The experiments described in Example 2 indicate that signaling pathways are not affected by T2 demonstrating the selective nature of T2 inhibition. Example 3 concerns results of studies on the effect of T2 in the treatment of patients with rheumatoid arthritis.

EXAMPLE 1

Effect of T2 on human lymphocyte function

This example describes the effect of T2 on in vitro immune responsiveness of human peripheral blood mononuclear cells (PBMC) obtained from normal individuals. It was found that T2 exerted a concentration-dependent profile of suppressive activity on both T cell and B cell functions, whereas the functional activities of monocytes were more resistant to the suppressive effects of T2.

Methods

Cell preparation. PMBC were obtained from the blood of healthy adults by centrifugation on sodium diatrizoate/Ficoll gradients (Sigma, St. Louis, MO). Monocutes were isolated from PBMC by centrifugation on Sepra-cell-MN (Sepratech, Oklahoma City, OK) or by glass adherence. The monocytes obtained from the two procedures were used to examine interleukin-1 (IL-1) production and antigen presentation, respectively. For purification of T cells and B cells, PBMC were incubated with Lleucine methyl ester HCl (Sigma) for 45 minutes at room temperature to deplete monocytes and natural killer cells, (Thiele et al., *J. Immunol.* 131:2282-2290, 1983). The resultant lymphocytes were rosetted with neuraminidase-treated sheep red blood cells (SRBC) and were then separated by Ficoll/diatrizoate centrifugation, (Rosenberg, et al., *J. Immunol.* 122:926-931, 1979). T cells were further purified by passage of the rosette-positive population over a nylon-wool column to remove residual B cells and monocytes, (Rosenstreich, et al., *J. Exp. Med.* 134:1170-1186, 1971). B cells were prepared from the initial population of rosette-negative cells by removing any remaining cells that formed rosettes with neuraminidase-treated SRBC.

Staining with monoclonal antibodies (MAb) to CD3 and CD20 and analysis with the fluorescence-activated cell sorter (FACS) indicated that the T cell and B cell populations were more than 96% and 90% pure, respectively. T cells were incubated with mitomycin c (0.1 mg/ml) for 45 minutes and then washed thoroughly, (Jelinek et al., *J. Immunol.* 136:83-92, 1986).

Reagents, T2, an chloroform/extract from the woody portion of the roots of TWH, was a kind gift of Taizhou Pharmaceutical Company (Taizhou, Jiang Su, People's Republic of China). It contained more than 8 different compounds including glycosides, diterpenoids, alkaloids, and ketones. Before use, the extract was dissolved in DMSO and further diluted with culture medium. Phytohemagglutinin (PHA; Wellcome Reagents, Research Triangle Park, NC), phorbol dibutyrate (PDB; Sigma), ionomycin (Calbiochem, San Diego, CA), and the anti-CD3 MAb, 64.1, were used for T cell activation (Geppert et al., *J Immunol* 138:1660-1666, 1987). MAb 64.1 was purified as previously described [Hansen et al., "T cell protocol", *Leukocyte Typing*. Edited by Bernard, et al. Berlin, Springer-Verlag, 1982]. Human recombinant interleukin-2 (rIL-2; Cetus, Emeryville, CA) and/or formalinized *Staphylococcus aureus* (SA; Calbiochem) was used for B cell activation. The MAb against the a chain of the IL-2 receptor (IL-2R), anti-Tac, was the gift of Dr. Thomas Waldmann (NIH, Bethesda, ND) and was used to analyze IL-2R expression. Interleukin-1 (Cistron Technology, Pine Brook, NJ) was purchased for standardization of the IL-1 assay. Affinity-purified goat anti-human IgA, IgG, and IgM and similar antibodies conjugated to horseradish peroxidase were purchased from Tago (Burlingame, CA). Streptokinase (SK) and tetanus toxoid (TT) were purchased from Hoechst-Roussel (Somerville, NJ) and MCDC Biologics (Jazaaica Plain, MA), respectively.

Cell culture and assay of lymphocyte DNA synthesis. T cells ($1 \times 10^5$/well) or B cells ($5 \times 10^4$/well) alone or B cells with mitomycin c-treated T cells ($1 \times 10^5$/well)

were cultured in RPMI 1640 medium (Hazleton Biologics, Lenexa, KS) supplemented with 10% fetal calf serum, penicillin G (200 units/ml), gentamicin (10 μg/ml), and L-glutamine (0.3 mg/ml) in 96-well microtiter plates in a total volume of 200 μl, with or without the stimuli indicated, and in the presence or absence of various concentrations of T2. The final concentration of DMSO in culture was 0.02–0.002%. This concentration of DMSO had no effect on any of the responses analyzed.

For both T and B cell activation, immobilized anti-CD3 (NAb 64.1) stimulation was used. This MAb was immobilized by incubating 50 μl (5 μg/ml) in each well for at least 2 hours at room temperature. The excess soluble antibody was removed before cell culture (Hansen, supra). Cells were cultured for the indicated duration, and then pulsed with 1 μCi of $^3$H-thymidine, ($^3$H-TdR; New England Nuclear, Boston, MA) for the last 12 and 18 hours for T cell and B cell cultures, respectively. $^3$H-TdR uptake was measured in a liquid scintillation counter. All data are expressed as the mean counts per minute of 3 replicate determinations (Davis et al., *J Immunol* 137:3758–3767, 1986).

IL-1 production assay. Monocutes (1×10$^5$/well) were suspended in RPMI 1640 medium with 1% normal human serum (NHS) and cultured with or without lipopolysaccharide (10 μg/ml) in the presence or absence of various concentrations of T2 for 24 hours. The culture supernatants were collected, and serial dilutions were assayed for IL-1 using C3H/HeJ murine thymocytes as described elsewhere (Moreno et al., *J Immunol* 136:3579–3587, 1986). Concentrations of T2 contained in the dilutions of supernatants had no effect on DNA synthesis by C3H/HeJ thymocytes.

IL-2 production assay. T cells (1×10$^5$/well) were incubated with or without PHA (1 μg/ml) or immobilized anti-CD3 in the presence or absence of various concentrations of T2 for 24 hours. Cell-free supernatants were harvested, serial dilutions were made, and IL-2 content was assayed with CTLL-2 cells as described previously (Gillis et al., *J Immunol* 120:2027–2032, 1978).

IL-2R expression. T cells were cultured with or without the indicated stimuli in the presence or absence of various concentrations of T2 for 36 hours. After washing, the cells were stained with saturating concentrations of anti-Tac or a mouse IgG control MAb, followed by fluorescein isothiocyanate-conjugated goat anti-mouse Ig antibody (Cappel, West Chester, PA). The samples were fixed with 1% paraformaldehyde and analyzed with a FACSTAR (Becton Dickinson, Mountain View, CA) flow cytometer, using a single-histogram statistics program (Davis, supra).

Measurement of Ig synthesis. The amount of IgG, IgA, and IgM in the culture supernatants of B cells stimulated with SA plus rIL-2 in the presence or absence of T2 for 7 days was determined using an isotype-specific enzyme-linked immunosorbent assay method. Quantitation of the Ig in the supernatants was then determined by comparison with a standard curve. The sensitivity of the assay is 15 ng/ml for IgA and IgG, and 30 ng/ml for IgN (Splawski et al., *J Immunol* 139:1432–1437, 1986).

Results

Figure 3:
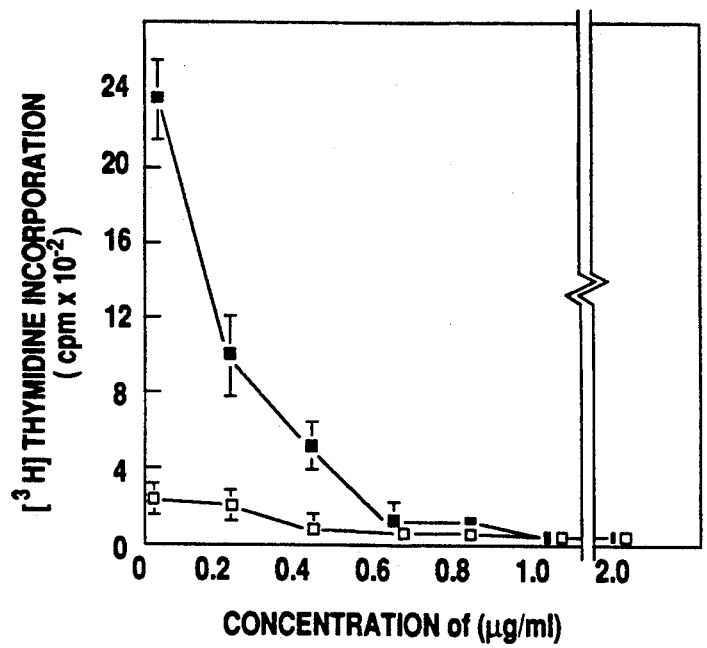
FIGS. 3. Inhibitory effect of T2 on IL-2 production. T cells ($1 \times 10^5$/well) were cultured with medium (□) or PHA (■) in the presence or absence of varying concentrations of T2 for 36 hrs. The cell-free supernatants were diluted 1:4 and analyzed for IL-2 activity with CTLL-2 cells. Mean [$^3$H]-TdR incorporation ±SEM of CTLL-2 cells from 6 experiments is shown.

Effect of T2 on human T cell responsiveness. These experiments noted that T2 caused concentration dependent inhibition of PHA induced $^3$H-thymidine incorporation by purified human T lymphocytes (FIG. 1). Fifty percent inhibition was noted at concentrations of approximately 0.2 μg per ml. Cell cycle analysis indicated that T2 prevented cells from progressing through the G1 phase of the cell cycle (FIG. 2). Mitogen induced IL-2 production by purified T Cells was also inhibited by a similar concentration of T2 (FIG. 3). Mitogen induced expression of IL-2 receptors was not inhibited by T2 (Table I) indicating that T2 is nontoxic to this cellular activity. These results suggested that the decrease in proliferation might be the result of inhibition of IL-2 production.

TABLE 1

EFFECT OF T2 ON INTERLEUKIN-2 (IL-2) RECEPTOR EXPRESSION*

| T2 | Nil | | PHA | |
|---|---|---|---|---|
| | % positive | Fluorescence intensity | % positive | Fluorescence intensity |
| 0 μg/ml | 10 ± 2 | 483 ± 18 | 65 ± 17 | 561 ± 166 |
| 0.65 μg/ml | — | — | 60 ± 22 | 519 ± 109 |
| 1.25 μg/ml | 9 ± 2 | 504 ± 29 | 61 ± 20 | 525 ± 128 |
| 2.50 μg/ml | — | — | — | — |

*T cells (1 × 10$^5$/well) were cultured with medium or phytohemagglutinin (PHA) in the presence or absence of various concentrations of T2 as indicated for 36 hours. Cells were collected, stained with anti-Tac monoclonal antibody followed by fluorescein isothiocyanate-conjugated goat anti-mouse IgG, and analyzed by flow cytometry. Values are the mean ± SEM of 6 experiments.

Figure 4:
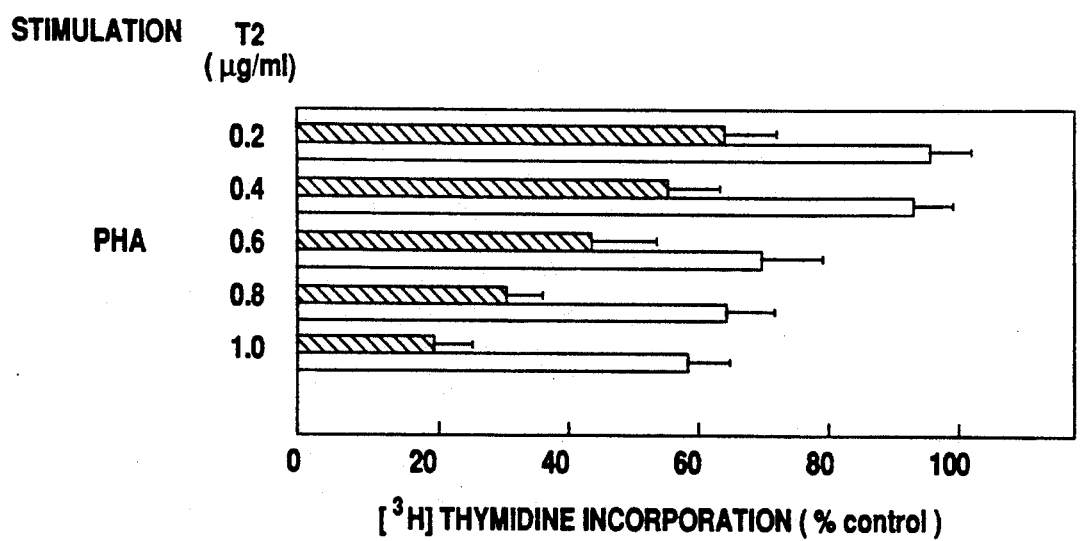
FIG. 4. Effect of supplemental IL-2 on T2 mediated inhibition of T cell proliferation. T cells ($1 \times 10^5$/well) were stimulated with PHA with (□) or without (■) IL-2 (10 U/ml) and in the presence or absence of varying concentrations of T2 for 3 days. The data are expressed as percent of control [$^3$H]-TdR incorporation from three experiments.
Figure 5:
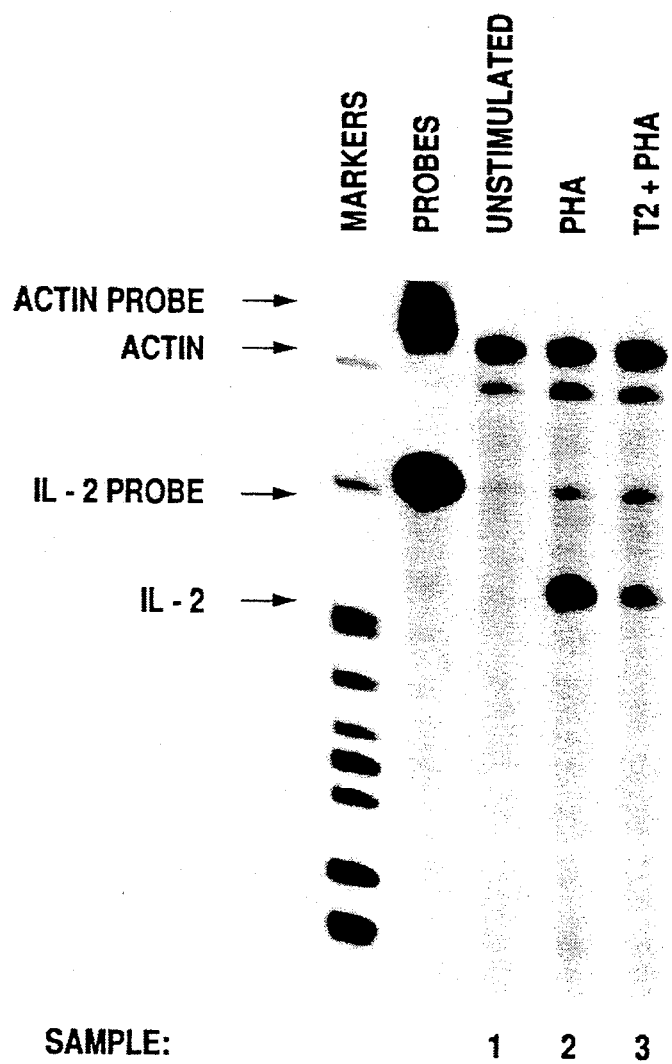
FIG. 5. Effect of T2 on steady state levels of IL-2 mRNA in mitogen stimulated T cells. T cells ($1 \times 10^6$/ml) were cultured with and without PHA in the presence or absence of T2 (1 µg/ml). After a 4-hour incubation, total RNA was isolated and IL-2 and actin mRNA levels determined by Si nuclease protection as described (54).

In order to examine IL-2 production, experiments were carried out in which the effect of T2 on proliferation was examined in the presence of supplemental IL-2. As can be seen in FIG. 4, much of the inhibitory effect of T2 was overcome by supplemental IL-2. These results suggested that one of the major actions of T2 was to inhibit IL-2 production. This appeared to result from an inhibition of IL-2 gene transcription since T2 inhibited the appearance of MMA for IL-2, as shown in FIG. 5. These experiments confirmed that one action of T2 was to inhibit IL-2 production.

Effect of T2 on human B lymphocyte responses.

Figure 6A:
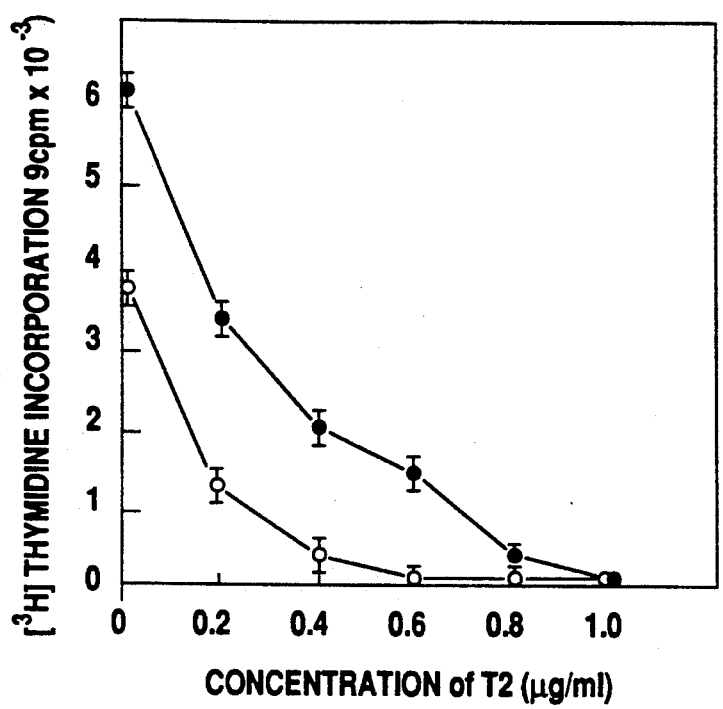
FIGS. 6A–6B. Effect of T2 on B cell DNA synthesis and Ig production.
Figure 6B:
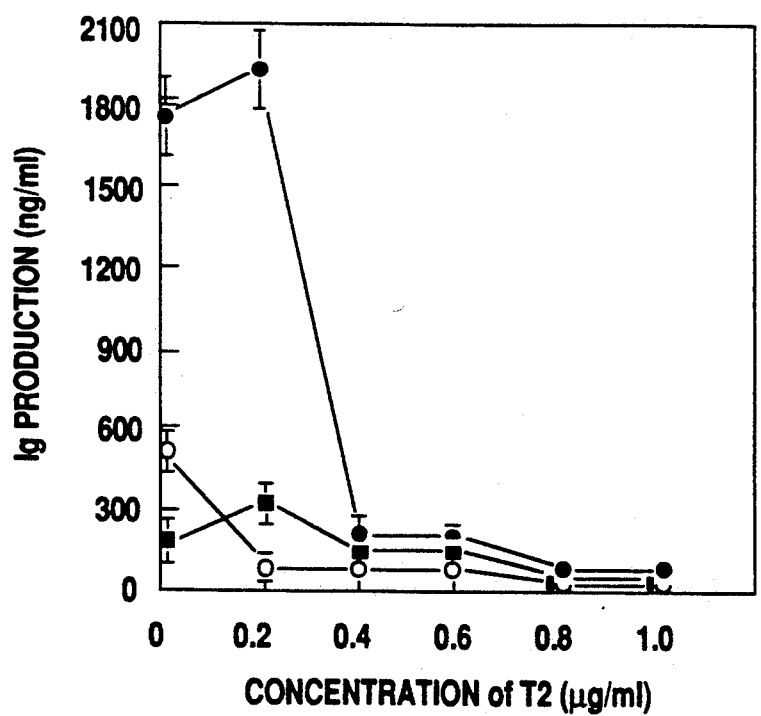

Additional effects of T2 were demonstrated when its action on human B cell responses was examined. As can be seen in FIGS. 6A–6B, T2 inhibited both mitogen-induced proliferation of highly purified B cells, as well as immunoglobulin production in a concentration dependent manner. These results suggested that T2 had additional effects beyond altering IL-2 production. Some specificity for the action of T2 was demonstrated, however, when its effects on a number of other cell types were examined. Thus, T2 had no effect on IL-1 production by human monocytes nor on their capacity to function as antigen presenting cells (49). In addition, T2 had no effect on the growth of endothelial cells or fibroblasts during a 48 hour culture. None of the inhibitory effects of T2 could be accounted for by non-specific toxicity, as inhibitory concentrations of T2 had no effect on the viability of either resting or stimulated lymphocytes, endothelial cells, fibroblasts, monocytes, or polymorphonuclear leukocytes. These results support the contention that T2 has a limited spectrum of immunosuppressive activity which cannot be accounted for by non-specific toxic effects. Of importance, the capacity of T2 to suppress both IL-2 production by T cells, and proliferation and immunoglobulin production by B cells could well explain the action of this agent in patients with RA.

EXAMPLE 2

Effect of T2 on critical signaling pathways.

The mechanism by which T2 might inhibit IL-2 production was examined in greater detail. The possibility was explored that T2 might inhibit a critical signaling pathway involved in inducing transcription of the IL-2 gene. Current information suggests that T cell receptor occupancy leads to activation of tyrosine kinases, followed by stimulation of phospholipase C. This results in production of phosphatidyl inositol triphosphate and diacylglycerol, that induce increases in intracellular calcium and activation of protein kinase C, respectively (50, 51, 52). Therefore, experiments were carried out to examine the possibility that T2 might inhibit one of these signaling pathways.

Methods

Effect of T2 on total IP generation by activated T cells. Fresh T cells (A) or Jurkat cells (B) were labeled with [$^3$H]-myoinositol overnight in the absence or presence of the indicated concentrations of T2. The cells were washed and incubated with 10 mM LiCl for 5 minutes then activated with PHA for 60 min. The cells were extracted with 0.75 ml of a 1:1 mixture of chloroform and reethanol, followed by 0.25 ml of chloroform and 0.25 ml of water. The phases were separated by centrifugation and the water soluble fractions were applied to a 0.25 ml Agl-X8 formate ion exchange column. Total inositol phosphate was eluted with 1.5 ml of 0.1M formic acid and 1M sodium formate. The radioactivity was quantified by scintillation counting. An aliquot of each cell population was also stimulated with PHA for 24 hours and supernatants assayed for IL-2 content using CTLL-2 cells.

Effect of T2 on the generation of IP fractions by PEA activated T cells. Jurkat cells were labeled with [$^3$H]-Myoinositol overnight in the presence or absence of various concentrations of T2. Following a 5 minute incubation with 10 mM LiCl, the cells were activated with PHA for 60 min. Water soluble IPs were isolated and quantitated. To accomplish this, the cultures were extracted with 0.75 ml of a 1:1 mixture of chloroform/reethanol, followed by 0.25 al each of chloroform and water. The phases were separated by centrifugation and the water soluble fraction was applied to a 0.25 ml Agl-X8 formate ion-exchange column, and washed extensively with 5 mM cold myoinositol. IP1, IP2 and IP3 were sequentially eluted with 4 ml of 0.2M ammonium formate plus 0.1M formic acid, 10 ml of 0.4M ammonium formate plus 0.1M formic acid and 10 ml of 1M ammonium formate plus 0.1M formic acid respectively. The radioactivity of the various elution fractions was quantified by scintillation counting.

Effect of T2 on DAG generation and IL-2 secretion by PEA stimulated T cells. T cells for each sample were cultured overnight with PHA in the presence or absence of the indicated concentrations of T2. The cell pellets were lysed with a mixture of chloroform and reethanol, and fractions separated with 1M NaCl and chloroform. The organic phase was collected and dried under nitrogen. DAG mass in the organic extract was assayed by solubilizing the lipid residues in a mixture of $^{32}$p-γ-ATP and DAG kinase and phosphatidic acid, incubating at 37° C. for 1 hour during which DAG was quantitatively converted to p-phosphatidic acid. The samples were dried and redissolved in chloroform. The solvent was applied to a silica gel and separated by thin layer chromatography with chloroform/methanol/acetic acid. After visualization with iodine, the spot which contained phosphatidic acid was harvested and radioactivity determined by liquid scintillation counting. An aliquot of cells was also stimulated with mitogen and supernatants harvested after 24 hours and assayed for IL-2 content.

Effect of T2 on tranalocation of PKC. Jurkat cells ($1 \times 10^6$/ml) were incubated overnight with or without T2 at the indicated concentrations. The cells were lysed by sonication and then cytoplasmic and membrane fractions separated by centrifugation. PKC activity in both the cytoplasmic and membrane fraction was assayed using a protein kinase C assay system (Amersham) which employed a synthetic peptide as a phosphate acceptor in the presence of phosphatidylserine, calcium and PMA.

Effect of T2 on protein tyrosine phosphorylation. Jurkat cells ($3 \times 10^6$) were incubated overnight in the absence or presence of the indicated concentrations of T2. The cells were washed and stimulated with PHA for 30 minutes. After centrifugation, the pelleted cells were solubilized with 1 x SDS sample buffer containing protease inhibitors. The lysates were centrifuged at 10,000 rpm for 15 minutes. The supernatants were analyzed for protein phosphorylation by western blotting using a mouse monoclonal antibody (Upstate Biotechnology, Inc.) against phosphotyrosine.

Results

Figure 7A:
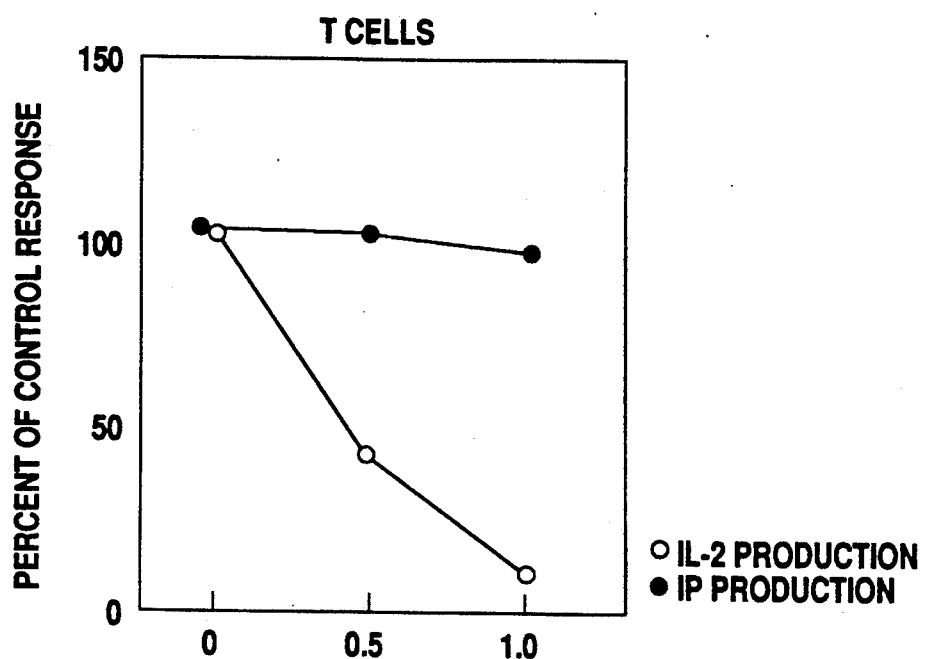
FIGS. 7A–7B. Effect of T2 on total IP generation by activated T cells. Fresh T cells (A) or Jurkat cells (B) were labeled with [$^3$H]-myo-inositol overnight in the absence or presence of the indicated concentrations of T2. Total IP was determined as described in Example 2. An aliquot of each cell population was also stimulated with PHA for 24 hours and supernatants assayed for IL-2 content using CTLL-2 cells (o). Data are the mean of three replicate experiments.
Figure 7B:
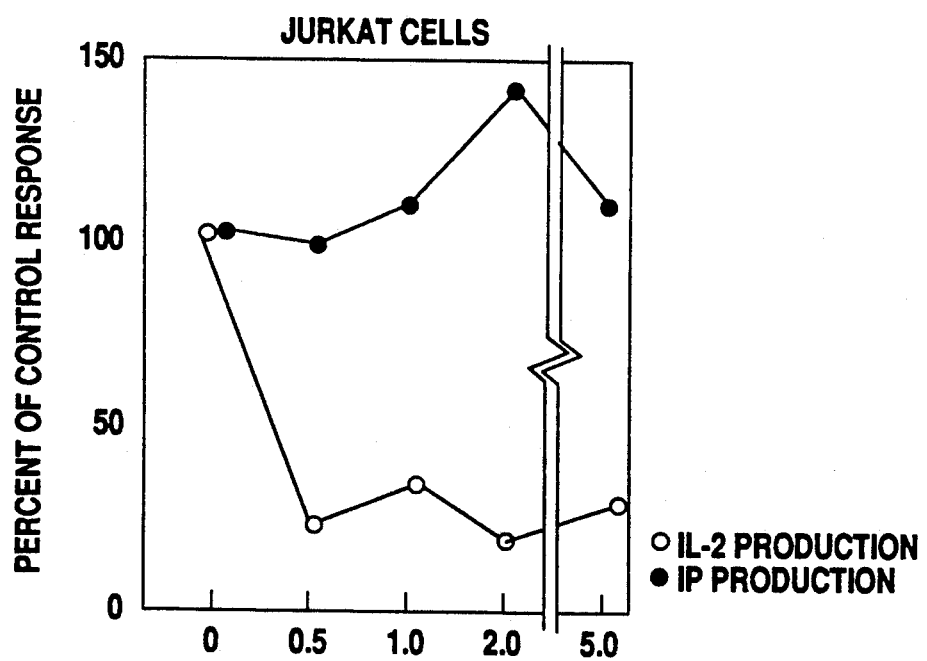
Figure 8A:
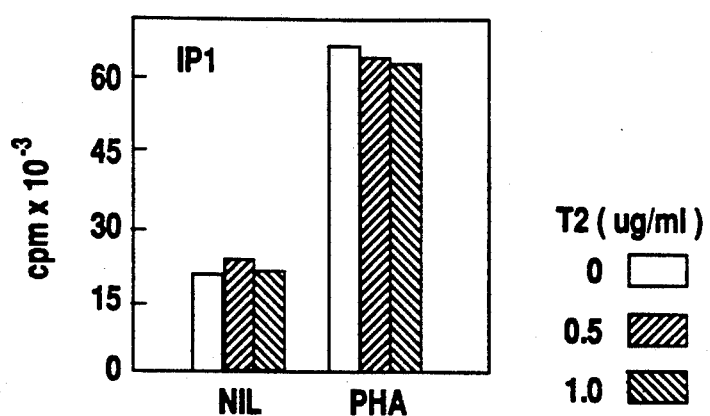
FIGS. 8A-8C. Effect of T2 on the generation of IP fractions by PHA activated T cells. Jurkat cells were labeled with [³H]-myoinositol overnight in the presence or absence of various concentrations of T2. Following a 5 minute incubation with 10 Mm LiCl, the cells were activated with PHA for 60 min. Water soluble IPs were isolated (IP1, FIG. 8A IP2, FIG. 8B and IP3, FIG. 8C and quantitated as described in Example 2. Data are from one of three similar experiments.
Figure 8B:
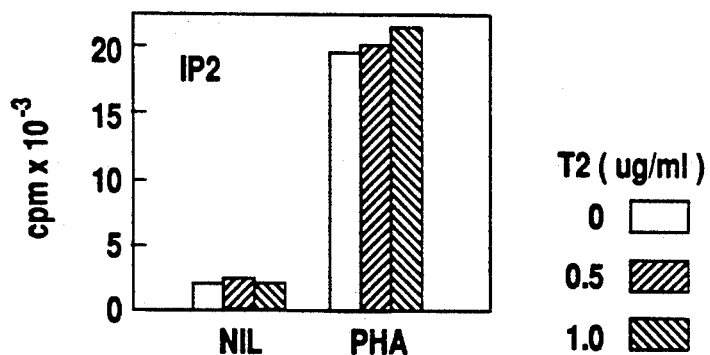
Figure 8C:
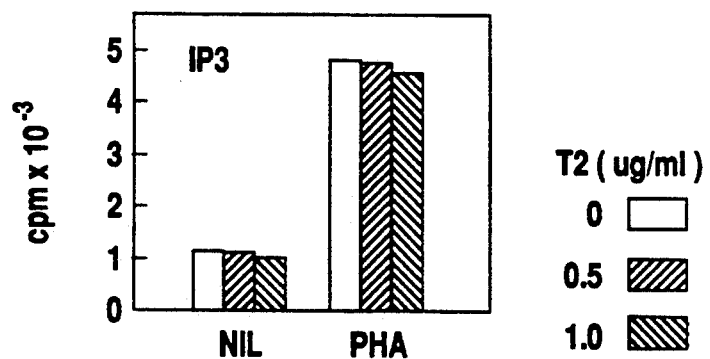
Figure 9:
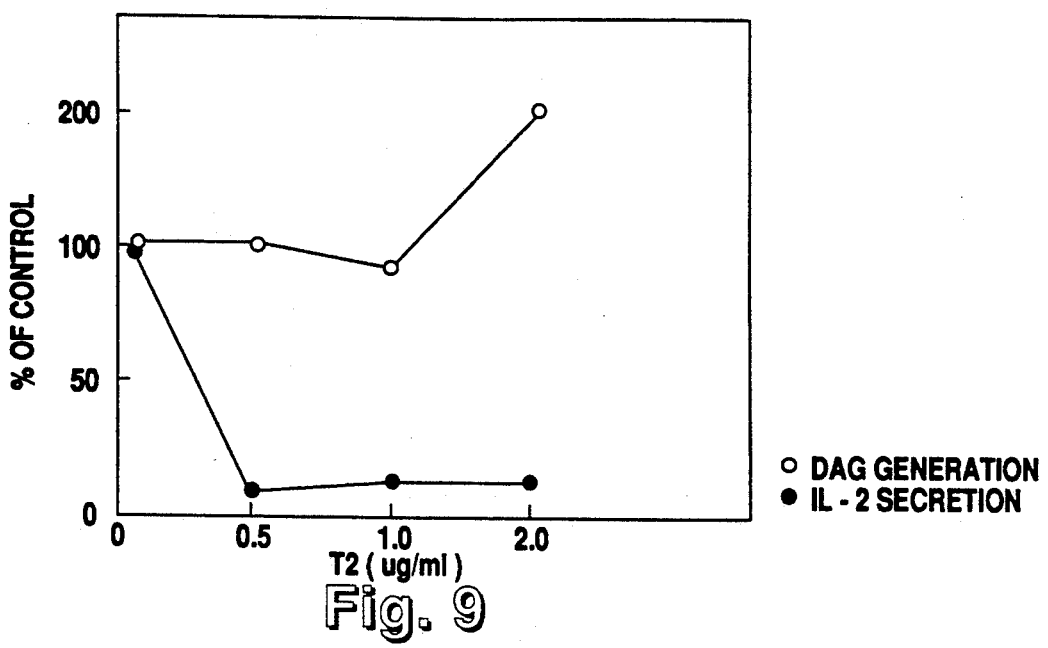
FIG. 9. Effect of T2 on DAG generation and IL-2 secretion by PHA stimulated T cells. DAG and IL-2 were assayed as described in Example 2. Data represent the mean of duplicate determination of three similar experiments.

The effect of T2 on mitogen induced production of phosphatidyl inositol metabolites. As can be seen in FIG. 7, mitogenic stimulation lead to the production of IL-2 and phosphatidyl inositol metabolites. Whereas IL-2 production was inhibited, generation of phosphatidyl inositol metabolites was not. Similar results were seen in fresh T cells and in the Jurkat leukemic T cell line. Additional experiments examined whether T2 specifically inhibited generation of IP3, which is thought to induce increases in intracellular calcium (52). As can be seen in FIG. 8, T2 had no effect on the generation of IP3 or other specific PI metabolites by mitogen activated T cells. Similar experiments examined the effect of T2 on the generation of diacylglycerol. As can be seen in FIG. 9, T2 inhibited IL-2 production from mitogen stimulated T cells, but had no effect on DAG production. Additional experiments, not shown, examined the activity of T2 on phospholipase C activity isolated from fresh T cells or Jurkat cells. Again, no inhibitory activity was observed. These experiments suggested that the action of T2 cannot be explained by an effect on these early signaling pathways. At these levels of T2 extract addition, nontoxicity to other cellular functions is established as indicated by these cellular assays.

Figure 10A:
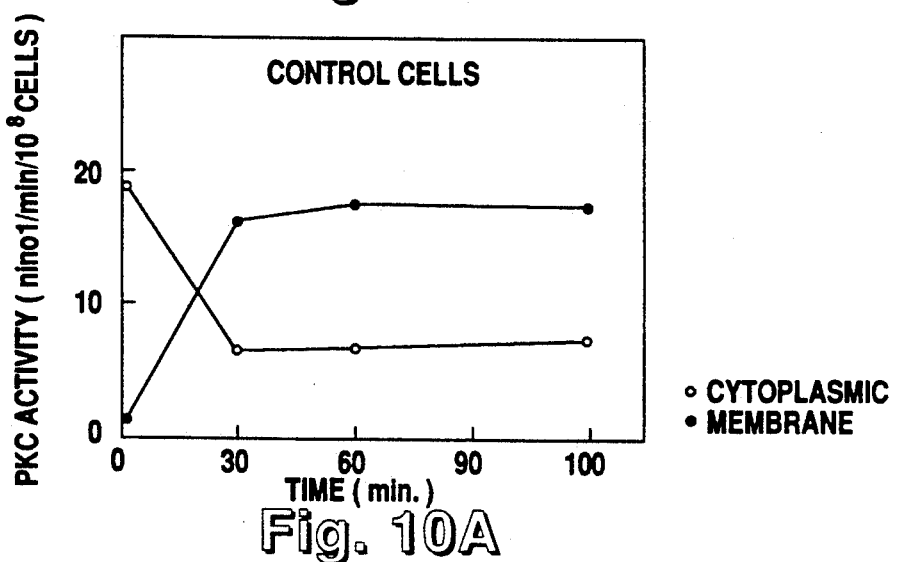
FIGS. 10A-10B. Effect of T2 on translocation of PKC. PKC activity in both the cytoplasmic FIG. 10A and membrane FIG. 10B fractions were assayed as described in Example 2.
Figure 10B:
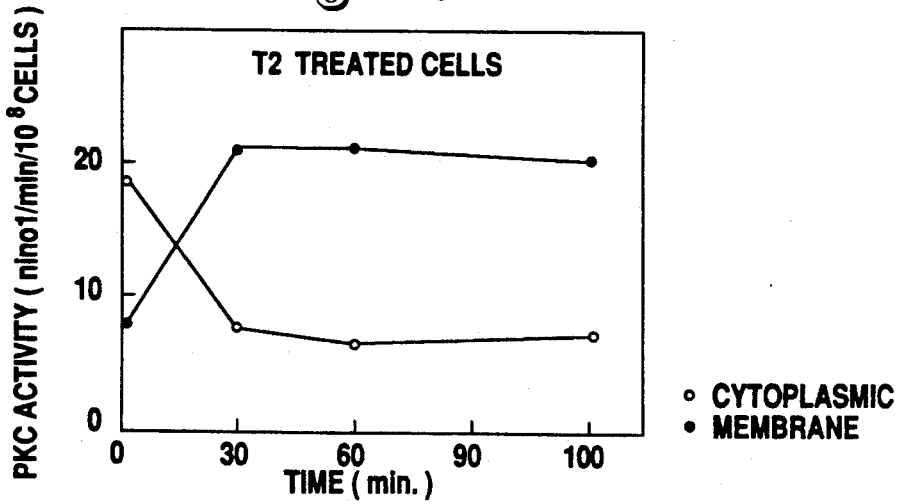
Figure 11:
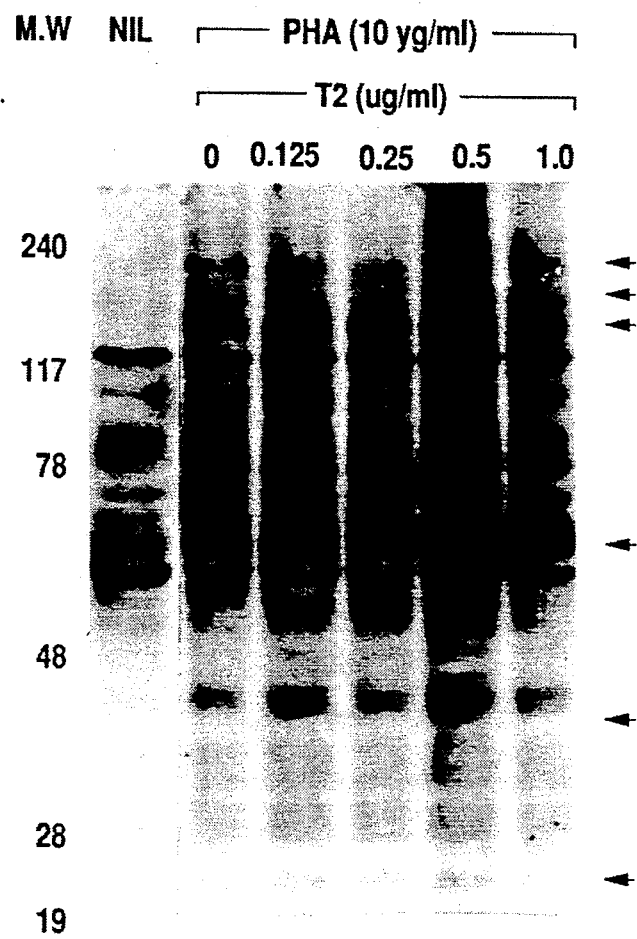
FIG. 11. Effect of T2 on Protein tyrosine phosphorylation. See Example 2 for methods. Arrows indicate tyrosine phosphorylation of new proteins after PHA stimulation.

The effect of T2 on protein kinase C activation. As can be seen in FIG. 10, mitogen stimulation led to translocation of PKC in Jurkat cells, and T2 did not effect PKC translocation. Finally, the effect of T2 on the activity of protein tyrosine kinase activity was explored. As can be seen in FIG. 11, mitogenic stimulation of T cells lead to phosphorylation of a number of protein species identified with a specific antibody to phosphotyrosine. However, T2 did not inhibit the activity of protein tyrosine kinase since the same bands were observed regardless of the presence of T2 during mitogenic stimulation. These experiments convincingly demonstrate that T2 has no effect on early signaling pathways involved in induction of IL-2 gene transcription.

EXAMPLE 3

In a preliminary open trial, it was found that a mixture of compounds (T2) extracted from *Tripterygium wilfordii Hook F* was effective in the treatment of rheumatoid arthritis.

To confirm the previous results obtained from these open studies, a prospective, controlled, double-blind cross-over study was designed and carried out in the outpatient clinic of Dr. Tao in Beijing, People's Republic of China.

The treatment plan was designed as follows:

Seventy patients with classic or definite adult-onset rheumatoid arthritis who had active disease for more than 6 months were accepted into the trial and randomly assigned to 2 treatment groups. Patients in Group A received T2 for a first course of treatment of 12 weeks, and then were subsequently changed to placebo for a second course of treatment of 4 weeks duration. Patients of Group B received placebo during the first course and then were crossed-over and received T2 therapy during the second course. T2 was taken in a dosage of 60 mg daily. Placebo tablets were identical in appearance to T2 tablets. Table 2 shows the treatment plan schedule.

TABLE 2

| TREATMENT PLAN (TOTAL COURSE: 16 WEEKS) | | |
|---|---|---|
| | First course treatment (12 weeks) | Second course treatment (4 weeks) |
| Group A | T2, 20 mg t.i.d. | Placebo |
| Group B | Placebo | T2, 20 mg t.i.d. |

All patients were assessed in an arthritis clinic every 4 weeks. The clinical assessment, overall assessment by physicians and drug distribution were carried out by individual doctors in a blinded manner. The laboratory assessments were done by technicians of a central hospital laboratory, who were also blinded to the details of the trial.

TABLE 3

| CLINICAL FEATURES OF PATIENTS ENTERING THE TRIAL | | | | |
|---|---|---|---|---|
| | First Treatment Course | | Second Treatment Course | |
| | Group A T2 | Group B Placebo | Group A Placebo | Group B T2 |
| Number of Patients | 35 | 35 | 27 | 31 |
| Male/Female | 3/32 | 4/31 | 1/26 | 4/27 |
| Mean age, years | 46.3 | 48.0 | 46.2 | 47.7 |
| Mean disease duration (years) | 5.9 | 6.1 | 5.8 | 6.0 |
| Stage of Disease | | | | |
| (1) | 6 | 6 | 4 | 5 |
| (2) | 14 | 16 | 11 | 13 |
| (3) | 12 | 10 | 10 | 9 |
| (4) | 3 | 3 | 2 | 4 |

The clinical features of patients entering the trial are shown in Table 3. Statistical analyses demonstrated that at the beginning of the trial, Group A and Group B did not differ from each other significantly in age, sex, duration of disease or stage of disease.

TABLE 4

| RESULTS OF A CONTROLLED TRIAL OF T2 IN RHEUMATOID ARTHRITIS | | | |
|---|---|---|---|
| | Number Beginning | No. of Patients Completing Treatment | |
| Group | Treatment | First Course (12 wks) | Second Course (4 wks) |
| A (T2 → Placebo) | 35 | 27 | 24 |
| B (Placebo → T2) | 35 | 31 | 25 |

As shown in Table 4, 27 patients of Group A completed the first course of treatment, of which 24 completed the second course. 31 and 25 of Group B completed the first course and second course of treatment, respectively.

Table 5 indicates the reasons patients withdrew from the study. Three patients of Group B but none of Group A withdrew from the trial because of worsening of disease during the first course of treatment, whereas 4 patients from Group A but none from Group B withdrew from the trial because of side effects.

TABLE 5

| REASONS FOR WITHDRAWAL FROM THE STUDY | | | | | | | | |
|---|---|---|---|---|---|---|---|---|
| | First Course Treatment | | | | Second Course Treatment | | | |
| | Group A T2 (n = 35) | | Group B Placebo (n = 35) | | Group A Placebo (n = 27) | | Group B T2 (n = 31) | |
| | No. | % | No. | % | No. | % | No. | % |
| Lost to follow up | 4 | 11 | 1 | 3 | 3 | 11 | 6 | 19 |
| Worsening of disease | 0 | 0 | 3 | 9 | 0 | 0 | 0 | 0 |
| Side effects | 4 | 11 | 0 | 0 | 0 | 0 | 0 | 0 |

Table 6 shows the therapeutic effects of the first course of treatment. In comparison with patients of Group B, patients of Group A showed significant improvement in all clinical assessments including morning stiffness, joint tenderness score, number of swollen joints, grip strength and 15 meter walking time.

TABLE 6

| CHANGES IN CLINICAL PARAMETERS IN PATIENTS COMPLETING THE FIRST COURSE OF TREATMENT | | | | |
|---|---|---|---|---|
| | | Group A T2 (n = 27) | Group B Placebo (n = 31) | *p |
| Morning stiffness (hours) | Before | 2.4 ± 0.4 | 1.1 ± 0.2 | 0.01 |
| | After | 0.9 ± 0.2 | 2.3 ± 1.4 | |
| Joint tenderness score | Before | 25.1 ± 1.9 | 25.5 ± 1.7 | 0.001 |
| | After | 7.9 ± 1.3 | 21.9 ± 2.1 | |
| Number of swollen joints | Before | 9.2 ± 0.9 | 7.8 ± 0.7 | 0.01 |
| | After | 4.3 ± 0.6 | 7.4 ± 1.1 | |
| Grip strength (mean of both sides, mm Hg) | Before | 49.0 ± 0.4 | 73.6 ± 7.7 | 0.05 |
| | After | 84.4 ± 7.5 | 81.2 ± 8.9 | |
| 15 meter walking time (second) | Before | 36.6 ± 6.6 | 37.0 ± 2.4 | 0.05 |
| | After | 21.6 ± 1.5 | 31.9 ± 3.6 | |

The most noteworthy improvement was observed in joint tenderness score, which improved from a mean of 25.1 before entry to a mean of 7.9 after the first course of treatment with T2. By contrast, there were no significant changes in this score in Group B patients treated with placebo.

As shown in Table 7, treatment with T2 also caused improvement in laboratory correlates of disease activity. Significant improvements in ESR, CRP and immunoglobulin levels were noted. The changes were significant at the p 0.001 level when compared between Group A and Group B.

TABLE 7
CHANGES IN LABORATORY PARAMETERS IN PATIENTS COMPLETING THE FIRST COURSE OF TREATMENT

|  |  | Group A T2 (n = 27) | Group B Placebo (n = 31) | *p |
|---|---|---|---|---|
| ESR (mm/hour) | Before | 69.2 ± 6.4 | 63.9 ± 5.2 | <0.001 |
|  | After | 41.0 ± 5.9 | 67.2 ± 6.6 |  |
| CRP (u/ml) | Before | 29.4 ± 5.7 | 31.6 ± 4.1 | <0.001 |
|  | After | 10.4 ± 3.9 | 43.7 ± 7.0 |  |
| RF (titers) | Before | 87.1 ± 23.2 | 86.1 ± 35.5 | NS |
|  | After | 48.0 ± 13.4 | 63.4 ± 10.9 |  |
| IgG (u/ml) | Before | 227.5 ± 4.6 | 231.9 ± 14.2 | <0.001 |
|  | After | 117.4 ± 9.5 | 180.4 ± 29.8 |  |
| IgM (u/ml) | Before | 302.8 ± 40.3 | 284.5 ± 32.2 | <0.001 |
|  | After | 105.2 ± 11.1 | 261.3 ± 29.3 |  |
| IgA (u/ml) | Before | 289.6 ± 29.4 | 257.6 ± 25.2 | <0.001 |
|  | After | 149.0 ± 15.5 | 280.4 ± 29.8 |  |

*Group A vs Group B

There was a greater tendency to decrease RF titer in T2 treated patients but the difference between the two groups after the first course of treatment was not statistically significant.

During the second course of therapy, patients who had received placebo initially improved significantly after 4 weeks of therapy with T2. (See Table 8). Significant improvements in joint tenderness score, number of swollen joints and grip strength were noted. Improvement in morning stiffness and 15 meter walking time were also noted, but these changes did not achieve statistical significance. Patients who had received T2 during the first 12 weeks of therapy continued to maintain improvement even after 4 weeks of placebo therapy during the second course.

TABLE 8
CHANGES IN CLINICAL PARAMETERS IN PATIENTS COMPLETING THE SECOND COURSE OF TREATMENT

|  |  | Group A Placebo (n = 24) | *p | Group B T2 (n = 25) | *p |
|---|---|---|---|---|---|
| Morning stiffness (hours) | Before | 1.8 ± 0.2 | NS | 2.5 ± 1.7 | NS |
|  | After | 0.8 ± 0.2 |  | 1.3 ± 0.9 |  |
| Joint tenderness score | Before | 7.9 ± 1.4 | NS | 22.2 ± 2.4 | <0.001 |
|  | After | 11.0 ± 2.6 |  | 13.5 ± 2.0 |  |
| Number of swollen joints | Before | 4.2 ± 0.8 | NS | 7.0 ± 1.2 | <0.05 |
|  | After | 4.4 ± 0.9 |  | 3.5 ± 0.5 |  |
| Grip strength (mean of both sides, mm Hg) | Before | 87.5 ± 8.0 | <0.05 | 80.1 ± 9.2 | <0.05 |
|  | After | 70.2 ± 9.5 |  | 97.1 ± 13.2 |  |
| 15 meter walking time (seconds) | Before | 20.3 ± 1.7 | NS | 31.5 ± 5.9 | NS |
|  | After | 17.1 ± 0.6 |  | 18.9 ± 2.3 |  |

*After vs before treatment

Aside from grip strength, no significant changes were observed in clinical assessments in Group A patients after 4 weeks of placebo treatment.

As shown in Table 9, significant decreases in ESR and RF titer were noted in Group B patients after the second course of treatment. No significant worsening in laboratory parameters were noted in Group A patients after 4 weeks of placebo therapy.

TABLE 9
CHANGES IN LABORATORY PARAMETERS IN PATIENTS COMPLETING THE SECOND COURSE OF TREATMENT

|  |  | Group A Placebo (n = 24) | *p | Group B T2 (n = 25) | *p |
|---|---|---|---|---|---|
| ESR (mm/hour) | Before | 42.3 ± 6.0 | NS | 68.5 ± 6.9 | <0.001 |
|  | After | 31.7 ± 7.3 |  | 22.0 ± 4.9 |  |
| RF (titer) | Before | 49.3 ± 13.5 | NS | 67.2 ± 12.1 | <0.05 |
|  | After | 32.0 ± 12.3 |  | 32.0 ± 19.1 |  |

*After vs before treatment

The overall effectiveness of T2 in the present trial was classified by its capacity to induce remissions, meaningful improvement or no therapeutic effect. (See Table 10).

TABLE 10
OVERALL EVALUATION OF THE PRESENT TRIAL

|  | First Course Treatment | | | | Second Course Treatment | | | |
|---|---|---|---|---|---|---|---|---|
| Clinical Response Compared to The Beginning of the Trial | Group A T2 (n = 27) | | Group B Placebo (n = 31) | | Group A Placebo (n = 24) | | Group B T2 (n = 25) | |
|  | No. | % | No. | % | No. | % | No. | % |
| Remission | 2 | 7.4 | 0 | 0 | 0 | 0 | 0 | 0 |
| Improvement |  |  |  |  |  |  |  |  |
| Patient's assessment | 25 | 93 | 7 | 23 | 20 | 82 | 20 | 80 |
| Physician's assessment | 25 | 93 | 7 | 23 | 19 | 79 | 22 | 88 |
| Clinical criteria | 22 | 82 | 7 | 23 | 19 | 79 | 11 | 44 |
| Laboratory evaluation | 23 | 85 | 4 | 13 | 18 | 75 | 13 | 52 |

Based on the therapeutic criteria for remission in RA developed by a subcommittee of the ARA, remission was observed in two patients of Group A at the end of the first course of treatment.

The percentage of patients who experienced meaningful improvements was significantly higher for Group A than for Group B patients as evaluated by physician's assessment, and clinical and laboratory evaluations after the first course of treatment.

The percent of Group B patients experiencing meaningful improvement after the second course of treatment was also remarkable, whereas improvement was maintained in Group A patients during the 4 week second course of placebo.

In order to determine whether T2 exerted an immunosuppressive effect in patients with RA, peripheral blood mononuclear cells (PBMC) were obtained from 18 patients of each group before and after the first course of treatment. These cells were cultured for 14 days and the amounts of IgM-RF and total IgM secreted were determined using a radioimmunoassay. (See Table 11).

TABLE 11

PRODUCTION OF IgM-RF AND TOTAL IgM BY PBMC OF PATIENTS AFTER THE FIRST COURSE OF TREATMENT

|     |        | Group A T2 (n = 18) | Group B Placebo (n = 18) | *p     |
| --- | ------ | ------------------- | ------------------------ | ------ |
| RF  | Before | 7.2 ± 3.2           | 5.4 ± 1.6                | <0.01  |
|     | After  | 1.5 ± 0.5           | 7.0 ± 2.2                |        |
| IgM | Before | 220.7 ± 53.6        | 260.5 ± 49.3             | <0.01  |
|     | After  | 151.9 ± 55.3        | 301.2 ± 100.5            |        |

*Group A vs Group B

In comparison with Group B, significant decreases in both IgM-RF and total IgM were noted in Group A after T2 treatment. These results suggest that T2 therapy had suppressed both IgM and IgM RF production in these patients and thus exerted an immunosuppressive effect.

As shown in Table 12, the most common side effects of T2 were dermal reactions including skin rash, cheilosis, thinning of skin and nails and pigmentation.

TABLE 12

INCIDENCE OF ADVERSE REACTIONS

|  | First Course Treatment | | | | Second Course Treatment | | | |
| --- | --- | --- | --- | --- | --- | --- | --- | --- |
|  | Group A T2 (n = 31) | | Group B Placebo (n = 31) | | Group A Placebo (n = 24) | | Group B T2 (n = 25) | |
|  | No. | % | No. | % | No. | % | No. | % |
| Skin rash & cheilosis | 15 | 39 | 1 | 3 | 0 | 0 | 7 | 28 |
| Diarrhea | 6 | 27 | 0 | 0 | 0 | 0 | 2 | 8 |
| Anorexia | 2 | 5 | 0 | 0 | 1 | 4 | 0 | 0 |
| Abdominal pain | 2 | 5 | 1 | 3 | 0 | 0 | 0 | 0 |
| Amenorrhea | 5/16 | 31 | 0 | 0 | 5/16 | 31 | 1/18 | 6 |
| Postmenopausal vaginal bleeding | 1/10 | 10 | 0 | 0 | 0 | 0 | 0 | 0 |

Although the incidence of skin reactions was quite high in Group A during the first course of treatment, none of the patients had to discontinue T2 treatment. Amenorrhea was another important side effect of T2. It was observed that 31% of female patients aged 49 or less having received T2 for 12 weeks developed amenorrhea whereas 6% of patients developed it after 4 weeks of T2 treatment. Amenorrhea disappeared in most patients when T2 was discontinued.

Figure 12:
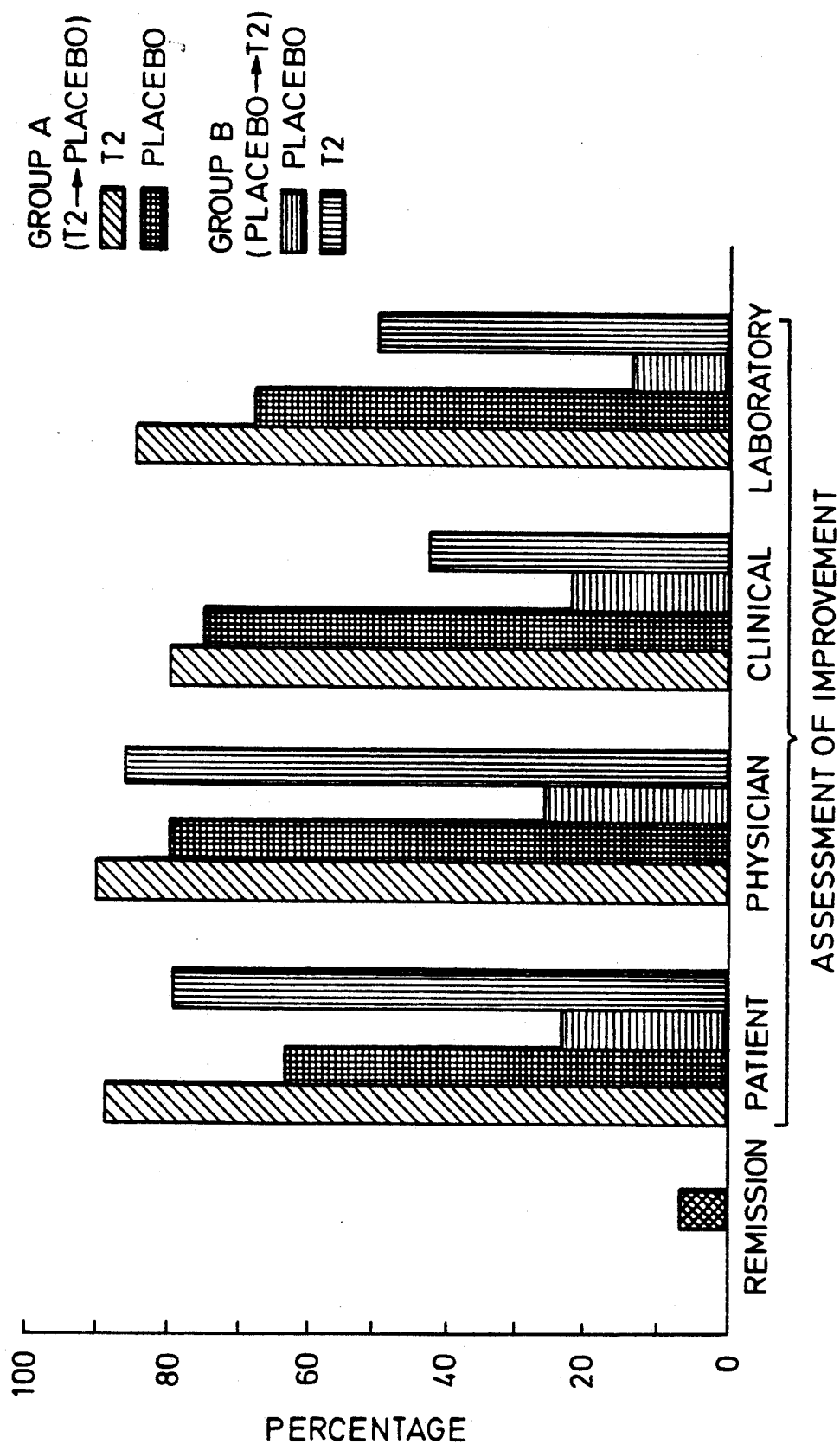
FIG. 12 summarizes assessment of symptomatic improvement in rheumatoid arthritis patients as a result of treatment with a mixture from *Tripterygium wilfordii Hook F*.

FIG. 12 summarizes the assessed improvements in symptoms of rheumatoid arthritis described above. T2 is an effective treatment for rheumatoid arthritis, significantly improving clinical manifestations and laboratory correlates of inflammation. Although toxicity was frequent, it necessitated cessation of therapy in few. clinical improvement was observed after only 4 weeks of therapy and persisted for at least 4 weeks after the medication was discontinued. T2 therapy suppresses the in vitro production of IgM and IgM rheumatoid factor.

T2 administration has also been shown to be effective in the treatment of systemic lupus erythematosus (Table 13). T2 appears to be effective in relieving acute clinical manifestations including joint inflammation, skin rash and renal disease (Table 13). A steroid sparing effect of T2 was also noted. In comparison with corticosteroids and commonly used immunosuppressive agents, such as cyclophosphamide, patients treated with T2 had fewer significant complications.

TABLE 13

THERAPEUTIC EFFECT OF T2 IN LUPUS NEPHRITIS

1. Patient group
   10 patients, aged 22-37, with duration of disease >1 year were treated with T2
2. Laboratory evaluation - before treatment
   +ANA: 10
   anti-DNA binding >20%: 9
   Proteinuria >3 g/24 h: 10
   Elevated serum creatinine: 3
3. Treatment plan:
   First month: T2 20 mg tid. Maintain prednisone <40 mg/day
   Followed by T2 10 mg tid. and tapered prednisone
   Total course of T2: 24 weeks
4. Results of treatment:
   Serum creatinine returned to normal in 2/3
   Proteinuria improved in 10/10:
   undetectable: 3
   <1 g/24 h: 3
   >1 g/24 h: 4
   Concomitant Medication
   3: withdrew from prednisone
   6: continued prednisone <10 mg/day
   1: changed to cyclophosphamide The following references and those cited in the text are incorporated in pertinent part by reference herein for the reasons cited in the specification.

EXAMPLE 4

Components of T2 extract and toxicity thereof

Figure 13:
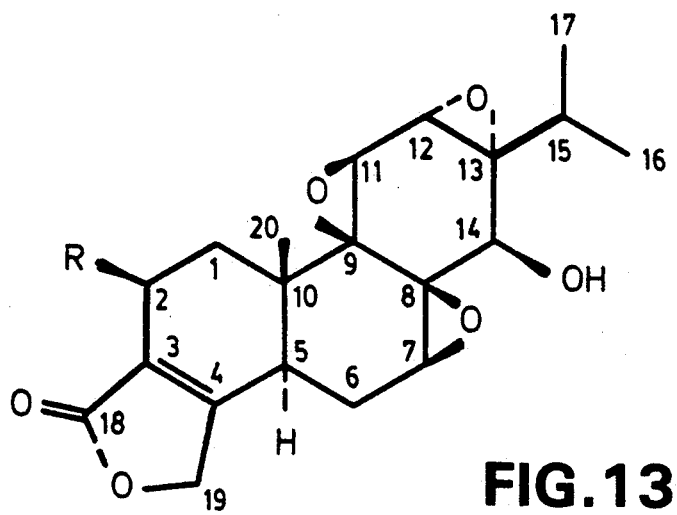
FIG. 13 schematically shows the structure of triptolide (1) and triptodiolide (2).
Figure 14:
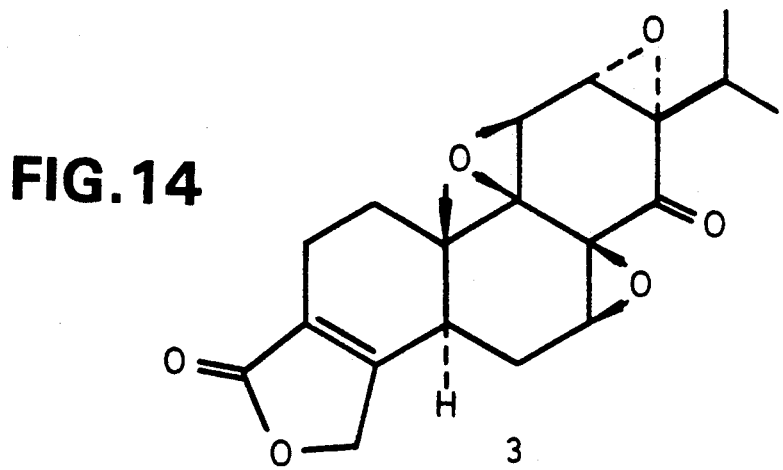
FIG. 14 schematically shows the structure of triptonide.
Figure 19:
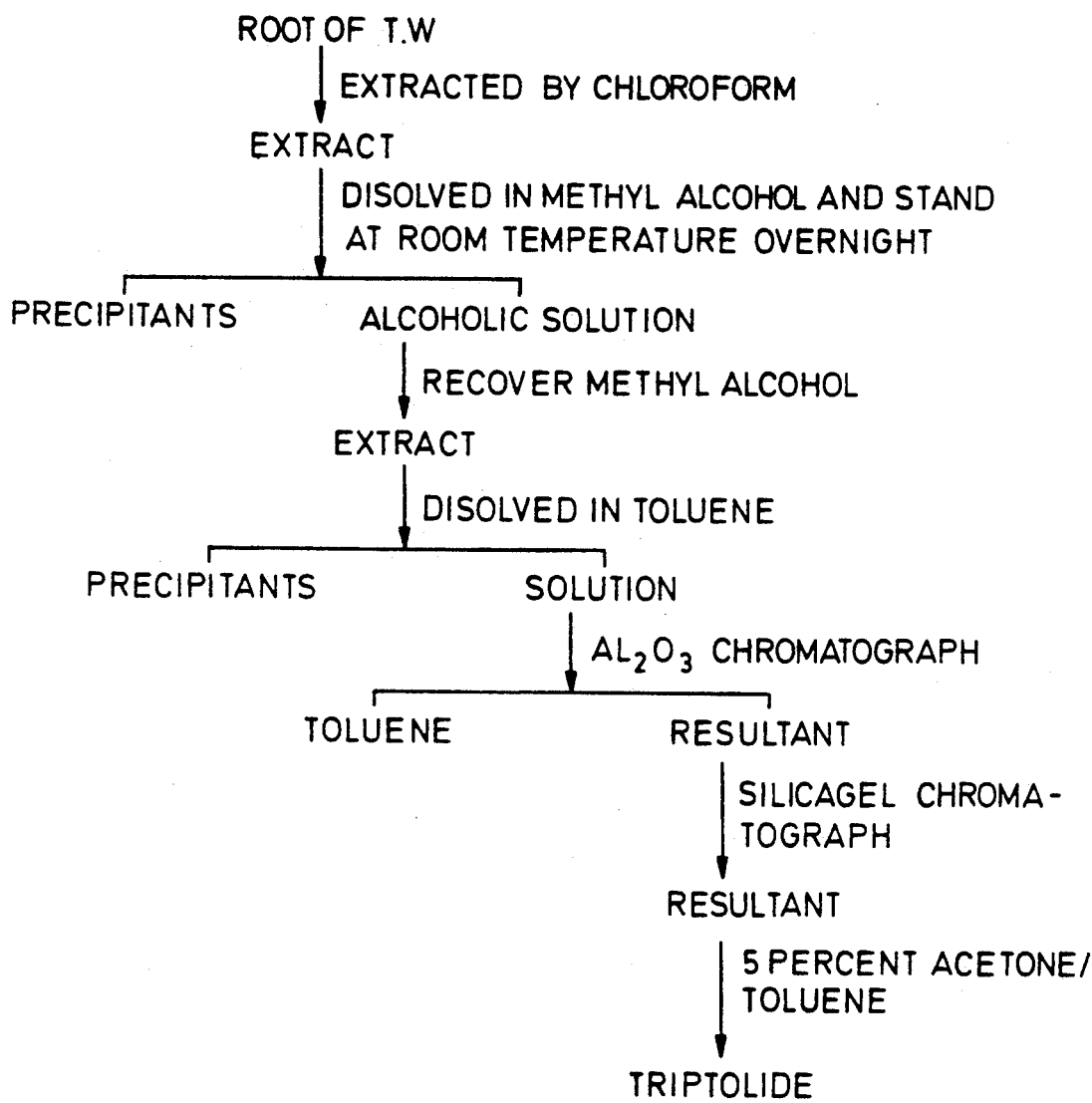
FIG. 19 outline the extraction procedure for preparation of triptolide.

The structure of triptolide and triptodiolide are shown in FIG. 13. FIG. 14 shows the structure of triptonide. Triptolide was isolated from alcoholic extracts of *Tripterygium wilfordii* Hook F by the method of Kupchan et al. (J. Am. Chem. Soc. 94, 7194-7195, 1972). This scheme for triptolide preparation is outlined in FIG. 19.

The effect of triptolide on immunopotent cells in vitro was determined as follows:

T cells, B cells and fibroblasts ($1 \times 10^6$/ml) were incubated with varying concentrations of T2 or triptolide for 72 hr. The cells were assayed for cell viability by using a cytoflowmeter (FACSCAN) after the cells were stained with propidium iodine. Table 14 demonstrates the effect of T2 or triptolide on cell viability.

TABLE 14

Effect of T2 or Triptolide on Cell Viability

| | | Inhibitors | | | | | | |
| --- | --- | --- | --- | --- | --- | --- | --- | --- |
| | | T2 (μg/ml) | | | | Triptolide (ng/ml) | | |
| Cell type | Control | 0.1 | 1.0 | 10.0 | 100.0 | 0.1 | 1.0 | 10.0 |
| | | (Percent viable cells) | | | | | | |
| T cells | 91.7 | 90.0 | 89.3 | 88.2 | 18.8 | 29.5 | 29.8 | 11.5 |
| B cells | 55.6 | 50.9 | 44.3 | 30.5 | 10.6 | 20.9 | 20.9 | 15.6 |
| Fibroblasts | 77.5 | 92.7 | 95.1 | 86.6 | 43.0 | 91.7 | 89.3 | 35.8 |

T2 at 100 μg/ml and triptolide at 10 ng/ml were toxic to fibroblasts indicating that at these levels, toxicity is nonspecific. At lower levels, suppression of T cell and B cell function is seen.

The capacity of triptolide to inhibit in vitro responses of human lymphocytes was examined. As can be seen in table 15, triptolide inhibited proliferation of both T and B lymphocytes profoundly at concentrations of 0.1-1.0 ng/ml.

TABLE 15

| Concentration of triptolide (ng/ml) | PHA-Induced T Cell DNA Synthesis ($^3$H-Thymidine Incorporation, CPM) | SA-Induced B Cell DNA Synthesis |
|---|---|---|
| 0 | 93,400 | 7,900 |
| 0.1 | 24,200 | 2,000 |
| 1.0 | 100 | 100 |

Figure 15:
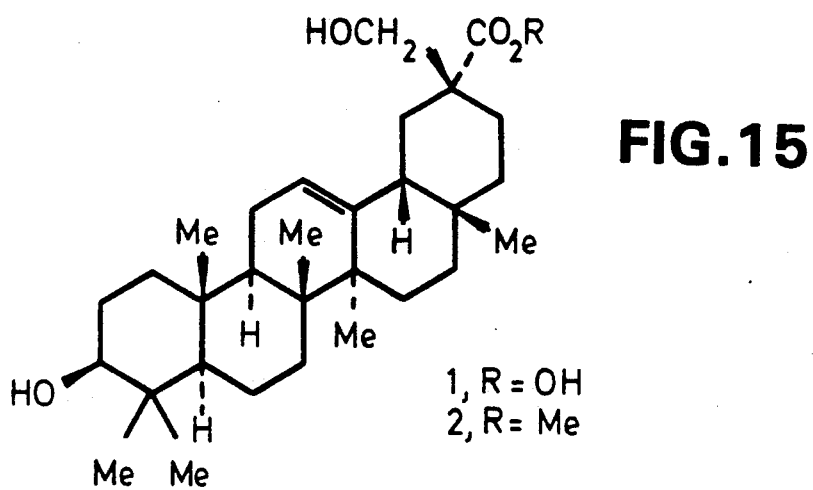
FIG. 15 schematically describes the structure of wilfortrine (1) and wilfortrine methyl ester (2).

Additional experiments indicated that this triptolide fraction also inhibited the in vitro production of immunoglobulin from mitogen stimulated human B lymphocytes at comparably small concentrations. These results support a conclusion that this triptolide fraction is extremely toxic, however, its specificity of action is yet to be determined. other components of *Tripterygium wilfordii* Hook F possibly having specific biological activity and thought to be useful individually or in combination in the practice of the present invention include:

polpunonic acid (wilfortrine) (1) and the methyl ester thereof (2) shown in FIG. 15 and described by Keng et al. (Chen. Abst. 107:55718y, p436, 1987);

triptophenolide (1) and triptophenolide methyl ether (2) shown in FIG. 16 and described by Wu et al. (Chem. Abst. 107:96917f, p712, 1987);

triptonoterpenol shown in FIG. 17 and described by Deng et al. (Chem. Abst. 107:112684k, p112692, 1987); and wilformine (shown in FIG. 18), wilforine, wilforgine, and wilforzine described by He et al. (Chem. Abst. 107:130906p, 1987;

Purified cozaponents of T2 will be administered to patients with autoimmune and inflammatory diseases including rheumatoid arthritis, systemic lupus erythematosus and psoriasis. Dosage will be determined based on the concentration of each component in the crude T2 mixture. After phase I dosage; escalation studies are carried out to evaluate toxicity, trials with non-toxic doses will be carried out to determine efficacy.

The following references are incorporated in pertinent part by reference herein for the reasons cited in the specification.

REFERENCES

1. Harris, E. D. (1990) "Rheumatoid Arthritis: Pathophysiology and implications for therapy" N. Engl. J. Med. 322:1277.
2. Lipsky, P. E. (1991) "Rheumatoid Arthritis" In Harrison's Principles of Internal Medicine, J. D. Wilson et al. editors, McGraw Hill, Inc., New York, pp. 1437-1443.
3. Kirkman et al. (1989) "Response to monoclonal CD7 antibody in rheumatoid arthritis" Lancet 1:589.
4. Kirkman et al. (1991) "Chimeric (human/mouse) CD7 monoclonal antibody treatment in rheumatoid arthritis" Brit. J. Rheumatol. 30 (Suppl 2):88.
5. Caperton et al. (1989) "Treatment of refractory rheumatoid arthritis (RA) with anti-lymphocyte immunotoxin" Arthritis Rheum. 24:2130.
6. Byers et al. (1990) "Patients with rheumatoid arthritis treated with a pan T-lymphocyte immunotoxin: phase II studies" FASEB J 4:A1855.
7. Strand et al. (1990) "Treatment of rheumatoid arthritis with an anti-CD5 immunoconjugate: clinical and immunologic findings and preliminary results of treatment" Arthritis Rheum. 33:S25.
8. Goldberg et al. (1990) "Preliminary trial of an anti-CD4 monoclonal antibody (MoAb) in rheumatoid arthritis (RA)" Arthritis Rheum. 33:S153.
9. Reiter et al. (1991) "Treatment of rheumatoid arthritis with monoclonal CD4 antibody M-T151" Arthritis Rheum. 34:524.
10. Herog et al. (1989) "Anti-CD4 antibody treatment of patients with rheumatoid arthritis: I. Effect on clinical course and circulating T cells" J. Autoimmunity 2:627.
11. Wassmer et al. (1990) "Therapy of rheumatoid arthritis with CD4 monoclonal antibodies" Arthritis Rheum. 33:2153.
12. Wendling et al. (1991) "Therapeutic use of monoclonal anti-CD4 antibody in RA" J. Rheumatol. 18:325.
13. Racadot et al. (1991) "Immunologic follow-up of 13 patients with rheumatoid arthritis treated by anti-CD4 monoclonal antibodies" Br. J. Rheum. 30(suppl 2):88.
14. Horneff et al. (1991) "Treatment of rheumatoid arthritis with an anti-CD4 monoclonal antibody" Arthritis Rheum. 34:129.
15. Moreland et al. (1991) "Treatment of refractory rheumatoid arthritis (RA) with a chimeric anti-CD4 monoclonal antibody" Clin. Res. 39:309A.
16. Kyle et al. (1989) "Beneficial effect of monoclonal antibody to interleukin 2 receptor on activated T cells in Rheumatoid arthritis" Ann. Rheum. Dis. 48:428.
17. Sewell et al. (1991) "Rapid improvement in refractory rheumatoid arthritis by an interleukin-2 receptor targeted immunotherapy" Clin. Res. 39:314A.
18. Jia Li (1985) "Chemistry and pharmacology and clinical application of plants of Tripterygium family" Yao Xue Tong Bao 20:101.
19. Toa at al. (1987) "Prospective, controlled, double-blind, cross-over trial of T2 (polyglycosides extracted from *Tripterygium wilfordii* Hook F) in the treatment of rheumatoid arthritis" Chinese J. Int. Med. 26:399.
20. Tao et al. (1988) "Mechanism of treatment of rheumatoid arthritis with *Tripterygium wilfordii* Hook F I. Effect of T2 on secretion of total IgM and IgM-RF by PBMC" Acta. Acad. Med. Sinicae 10:361.
21. Tao et al. (1989) "A prospective, controlled, double blind, cross-over study of *Tripterygium wilfordii* Hook F in the treatment of rheumatoid arthritis" Chinese Med. J. 102(5):327.
22. (1982) "T2 Study Group of Jiang Su Province of China: Summary of the clinical trials of T2 in the treatment of 554 patients with various diseases." Annals Chinese Acad. Med. Sci. 3:3.
23. DeYong, Y (1983) "Clinical observation of 144 cases of rheumatoid arthritis treated with glycoside of radix *Tripterygium wilfordii*" J. Trad. Chinese Med. 3(2):125.
24. Xue, Z (1984) "Treatment of 21 cases of systemic lupus erythematosus (SLE) with *Tripterygium wilfordii*" Chinese J. Derm 17(3):201.
25. (1979) "T2 Study Group of Chinese Institute of Dermatology: Clinical observation on the treatment of skin disorders with polyglycoside of *Tripterygium wilfordii*" Acta. Acad. Med. Sinicae 1(2):6.
26. Xie, D (1983) "Experience in the treatment of Behcet's disease with polyglycosides of *Tripterygium wilfordii* Hook" Zhong Xi Yi Jie HE ZA Zhi 3(6):349.
27. Peng, S (1983) "Report on 20 patients with Henoch-Schonlein purpura treated with polyglycosides of *Tripterygium wilfordii* Hook (T2)" Jian Su Yi Yao 11:38.
28. Feng, B (1985) "Observation on the effect of polyglycosides of *Tripterygium wilfordii* Hook (T2) on 50 cases of leprosy reactive status" Chinese Clin. Derm. J. 4:211.
29. Wu, Y (1986) "Treatment of neuralgia of leprosy reactive status with polyglycosides of *Tripterygium wilfordii* Hook (T2)" Chinese J. Derm. 19(4):217.
30. Jiang, X (1982) "Exploration of the treatment of nephrotic syndrome with polyglycosides of *Tripterygium wilfordii* Hook (T2)" Chinese J. Ped 20(4):201.
31. Li, X (1982) "Clinical observation on the treatment of 53 cases of nephrotic syndrome with polyglycosides of *Tripterygium wilfordii* Hook (T2)" Chinese J. Ped. 20(4):203.
32. Qian, J (1987) "Observation on the effect of polyglycosides of *Tripterygium wilfordii* Hook (T2) on idiopathic IgA nephrology" Annual Meeting of Nephrology (People's Republic of China).
33. Li, X (1987) "Treatment of 50 cases of children's purpura nephritis with polyglycosides of *Tripterygium wilfordii* Hook" Jiang Su Yi Yao 12:644.
34. Pan, Y (1987) "Treatment of purpura nephritis with *Tripterygium wilfordii* Hook" Acta. Acad. Med. Sinicae 9(6):2.
35. Cheng. R (1988) "Observation of the therapeutic effect of polyglycosides of *Tripterygium wilfordii* Hook (T2)

REFERENCES -continued combined with thyroid gland tablets on chronic lymphocytic thyroiditis" Zhong Xi Yi Jie He Za Zhi 8(11):676.
36. Hubei Study Group (1982) "Pharmacological study on the ethanol extract of *Tripterygium wilfordii* Hook F" Zung Cao Yao 13:27.
37. Wei et al. (1988) "Side effects of T2 in the treatment of 106 patients with glomerular diseases" New Drug and It's Clinical Application 1(6):37.
38. Jiang et al. (1987) "*Tripterygium wilfordii* Hook caused acute toxicity with kidney involvement in 17 cases" Chinese J. Kidney Dis 3(3):167.
39. Chen et al. (1987) Clinical analysis of 10 cases of *Tripterygium wilfordii* Hook caused toxicity" Symposium, "Clinical Application of *Tripterygium wilfordii* Hook", Hubei, China.
40. Zheng et al. (1983) "Studies on toxicity of total glycosides in *Tripterygium wilfordii*" Acta. Acad. Med. Sinicae 5(2):73.
41. Zheng et al. (1983) "Studies on pharmacological actions of total glycosides in *Tripterygium wilfordii* Hook F" Acta. Acad. Med. Sinicae 5:1.
42. Chang et al. (1984) "A preliminary study of the immunosuppressive activity of mixed glycosides of *Tripterygium wilfordii* Hook F" Chinese J. Immunol. 4:331.
43. Zheng et al. (1982) "Effect of the decoction of *Tripterygium wilfordii* Hook on immune functions" Fujiang Med. J. 4: 222.
44. Zuo et al. (1986) "Different effect of *Tripterygium reglii* on T and B cell function" Chinese J. Immunol. 2:232.
45. Zhang et al. (1983) "Studies on diterpenoids from *Tripterygium wilfordii*" Acta. Acad. Med. Shanghai 13:267.
46. Zhang, LS (1986) "Inhibitory effect of celastrol on murine lymphocyte proliferation" Acta. Pharmacol. Sinicae 7:85.
47. Zhang et al. (1981) "Antineoplastic action of triptolide and its effect on the immunologic function in mice" Acta. Pharmacol. Sinicae 2(2):128.
48. Kupchan, SM (1976) "Novel plant-derived tumor inhibitors and their mechanisms of action" Cancer Treatment Reports 60:1115.
49. Tao rt al. (1991) "The effect of an extract of Chinese herbal remedy *Tripterygium wilfordii* Hook F on human immune responses" Arthritis & Rheum. in press.
50. June et al. (1990) "Increases in tyrosine phosphorylation are detectable before phospholipase C activation after T cell receptor stimulation" J. Immunol. 44: 1591.
51. Mustelin et al. (1990) "T cell antigen receptor-mediated activation of phospholipase C requires tyrosine phosphorylation" Science 247:1584.
52. Weiss et al. (1986) "The role of the T3/antigen receptor complex in T cell activation" Ann. Rev. Immunol. 4:593.
53 Zalkow et al. (1988) "Macrocyclic pyrrolizidine alkaloids from Senecio anononymus. Separation of a complex alkaloid extract using droplet countercurrent chromatography" J. Nat. Prod. 31:1520.
54. Minakuchi et al. (1990) "Delineation of the mechanisms of inhibition of human T cell activation by $PGE_2$" J. Immunol. 145:2616.

What is claimed is:

1. A method for inhibiting interleukin-2-mediated immunosuppression comprising administering a preparation consisting essentially of a *Tripterygium Wilfordii* Hook F root extract in a therapeutically effective amount to a patient in need of such treatment; and inhibiting interleukin-2 mediated immunosuppression in the patient.

2. A method for suppressing interleukin-2 in autoimmune disease comprising administering a preparation consisting essentially of *Tripterygium Wilfordii* Hook F root extract, in a therapeutically effective amount to a patient having an autoimmune disease sufficient to suppress interleukin-2 production.

3. The method of claim 2 wherein the autoimmune disease is rheumatoid arthritis, systemic lupus erythematosus or psoriasis.

4. A method of inhibiting interleukin-2 mediated immunoglobulin systhesis comprising administering a preparation consisting essentially of a *Tripterygium Wilfordii Hook F* root extract in a therapeutically effective amount sufficient to inhibit interleukin-2 production to a patient in need of such treatment.

5. A method of inhibiting interleukin-2 mediated cell proliferation of human peripheral blood lymphocytes comprising administering a preparation consisting essentially of a *Tripterygium Wilfordii Hook F* root extract in a therapeutically effective amount sufficient to inhibit interleukin-2 production to a patient in need of such treatment.

6. A method of inhibiting interleukin 2-mediated cellular immune responses comprising administering a preparation consisting essentially of a *Tripterygium Wilfordii Hook F* root extract in a therapeutically effective amount sufficient to inhibit interleukin-2 production to a patient in need of such treatment.

7. A method of selectively inhibiting the production of interleukin-2 comprising administering a preparation consisting essentially of a *Tripterygium Wilfordii Hook F* root extract in a therapeutically effective amount sufficient to inhibit interleukin-2 production to a patient in need of such treatment.

8. The method of claim 1, 2, 4, 5, 6, or 7 wherein the therapeutically effective amount is about 60 mg/day.

9. The method of claim 1, 2, 4, 5, 6 or 7 wherein the lack of substantial cellular toxicity is measured by substantially unchanged interleukin-2 receptor expression or cellular signaling activity.

10. The method of claim 9 wherein the cellular signaling activity is inositol triphosphate production, diacylglycerol generation, translocation of protein kinase C or protein tyrosine kinase activity.

* * * * *

UNITED STATES PATENT AND TRADEMARK OFFICE
CERTIFICATE OF CORRECTION

PATENT NO.  : 5,294,443
DATED       : March 15, 1994
INVENTOR(S) : Lipsky et al.

It is certified that error appears in the above-indentified patent and that said Letters Patent is hereby corrected as shown below:

On the title page, item (54), line 1, delete "WILFORD II" and substitute --WILFORDII--, therefore.

In claim 4, column 20, line 18, delete "systhesis" and substitute --synthesis--, therefore.

In claim 9, column 20, line 45, delete "lack of" and substitute --extract lacks--, therefore.

In claim 9, column 20, line 45, delete "is" and substitute --as--, therefore.

Signed and Sealed this

Thirteenth Day of September, 1994

Attest:

BRUCE LEHMAN

Attesting Officer

Commissioner of Patents and Trademarks